United States Patent
Zhou et al.

(10) Patent No.: US 10,538,594 B2
(45) Date of Patent: Jan. 21, 2020

(54) METHODS FOR PHRASING EPIGENETIC MODIFICATIONS OF GENOMES

(71) Applicant: CENTRILLION TECHNOLOGY HOLDINGS CORPORATION, Grand Cayman (KY)

(72) Inventors: Wei Zhou, Saratoga, CA (US); Jeremy Edwards, Albuquerque, NM (US); Justin Costa, Union City, CA (US)

(73) Assignee: Centrillion Technology Holdings Corporation (KY)

( * ) Notice: Subject to any disclaimer, the term of this patent is extended or adjusted under 35 U.S.C. 154(b) by 147 days.

(21) Appl. No.: 15/560,722

(22) PCT Filed: Apr. 6, 2016

(86) PCT No.: PCT/US2016/026157
§ 371 (c)(1),
(2) Date: Sep. 22, 2017

(87) PCT Pub. No.: WO2016/164419
PCT Pub. Date: Oct. 13, 2016

(65) Prior Publication Data
US 2018/0112010 A1    Apr. 26, 2018

Related U.S. Application Data

(60) Provisional application No. 62/143,722, filed on Apr. 6, 2015.

(51) Int. Cl.
*C12Q 1/6804* (2018.01)
*C12N 15/10* (2006.01)
(Continued)

(52) U.S. Cl.
CPC .............. *C07K 16/44* (2013.01); *C07K 16/46* (2013.01); *C12N 15/1006* (2013.01);
(Continued)

(58) Field of Classification Search
None
See application file for complete search history.

(56) References Cited

U.S. PATENT DOCUMENTS

| 7,670,770 B2 | 3/2010 | Chou et al. |
| 9,328,382 B2 | 5/2016 | Drmanac et al. |

(Continued)

FOREIGN PATENT DOCUMENTS

| WO | WO-2012106546 A2 | 8/2012 |
| WO | WO-2012106546 A3 | 11/2013 |

(Continued)

OTHER PUBLICATIONS

Adey et al. RApid Low-input Low-Bias construction of shotgun fragment libraries by high-density in vitro transportation. Genome Biology Dec. 1, 2010 11:1-7.

(Continued)

*Primary Examiner* — Kaijiang Zhang
(74) *Attorney, Agent, or Firm* — Wilson Sonsini Goodrich & Rosati

(57) ABSTRACT

Provided herein are methods and compositions for analyzing epigenetic modifications of genomes. The methods and compositions are suited for complete epigenome sequencing of any modification for which an antibody or an affinity binding agent has been developed. In one aspect, provided herein is a method for analyzing epigenetic modification of a genome. In some embodiments of aspects provided herein, the method further comprises sequencing a sequencing library to generate sequence reads, and assembling the sequence reads with aid of a positional barcode sequence information. In some embodiments of aspects provided herein, the method further comprises determining a location of at least two different epigenetic modifications of the nucleic acid. Another aspect of the present disclosure pro- (Continued)

vides a kit for analyzing an epigenetic modification of a nucleic acid.

14 Claims, 11 Drawing Sheets

(51) Int. Cl.
| | |
|---|---|
| *C12Q 1/6811* | (2018.01) |
| *C12Q 1/6874* | (2018.01) |
| *C07K 16/44* | (2006.01) |
| *C07K 16/46* | (2006.01) |

(52) U.S. Cl.
CPC ..... *C12N 15/1065* (2013.01); *C12N 15/1093* (2013.01); *C12Q 1/6804* (2013.01); *C12Q 1/6811* (2013.01); *C07K 2317/92* (2013.01); *C07K 2319/01* (2013.01); *C07K 2319/20* (2013.01); *C12Q 1/6874* (2013.01); *C12Q 2523/303* (2013.01); *C12Q 2535/122* (2013.01); *C12Q 2537/164* (2013.01); *C12Q 2565/501* (2013.01); *C12Q 2600/156* (2013.01)

(56) References Cited

U.S. PATENT DOCUMENTS

| | | | |
|---|---|---|---|
| 2013/0017978 A1* | 1/2013 | Kavanagh et al. | ........................ C12N 15/1093 506/26 |
| 2013/0172216 A1* | 7/2013 | Mir | ..................... C12Q 1/6818 506/26 |
| 2014/0186940 A1 | 7/2014 | Goel | |
| 2014/0220160 A1* | 8/2014 | Cinque et al. | ....... C12Q 1/6806 424/649 |
| 2016/0046985 A1 | 2/2016 | Drmanac et al. | |
| 2016/0168632 A1 | 6/2016 | Edwards | |
| 2017/0022554 A1 | 1/2017 | Drmanac et al. | |

FOREIGN PATENT DOCUMENTS

| | | | |
|---|---|---|---|
| WO | WO-2015017759 A1 * | 2/2015 | ........... C12Q 1/6825 |
| WO | WO-2015085268 A1 | 6/2015 | |
| WO | WO-2015085274 A1 | 6/2015 | |
| WO | WO-2015085275 A2 | 6/2015 | |
| WO | WO-2015085275 A3 | 9/2015 | |
| WO | WO-2016164419 A1 | 10/2016 | |

OTHER PUBLICATIONS

Ananiev et al. Optical mapping discerns genome wide DNA methylation profiles. BMC Molecular Biology 2008 9:68. 14 pages.

Baer et al. Genome-Wide Epigenetic Regulation of miRNAs in Cancer. Cancer Res, 73(2):473-477 (2013).

Calcagno et al. DNA and histone methylation in gastric carcinogenesis. World J Gastroenterol Feb. 28, 2013. 19(8):1182-1192.

Clark et al. Characterization of DNA methyltransferase specificities using single-molecule real-time DNA sequencing. Nucleic Acids Research 2012 40(4):e29. 12 pages. doi:10.1093/nar/gkr1146. Published online Dec. 7, 2011.

Fang et al. Genome-wide mapping of methylated adenine residues in pathogenic *Escherichia coli* using single-molecule real-time sequencing. Nature Biotechnology vol. 30 pp. 1232-1239 (2012).

Ferree et al. Electrokinetic stretching of tethered DNA Biophys. J. 85(4):2539-46 2003.

Flusberg et al. Direct detection of DNA methylation during single-molecule real-time sequencing. Nat Methods. Jun. 2010;7(6):461-5. doi: 10.1038/nmeth.1459. Epub May 9, 2010.

International Search Report and Written Opinion dated Jul. 12, 2016 for International Application No. PCT/US2016/026157.

Levy-Sakin et al. Towards single-molecule optical mapping of the epigenome. ACS Nano. Jan. 28, 2014.

Lim et al. DNA methylation profiling in nanochannels. Biomicrofluidics. Dec. 1, 2011, 5:1-8.

Song et al. Sensitive and specific single-molecule sequencing of 5-hydroxymethylcytosine. Nature Methods, 9:75-77 (2013).

Wang et al. Stretching DNA with Optical Tweezers. Biophysical Journal 72:1335-1346 (1997).

Aline Cerf et al., "Ordered Arrays of Native Chromatin Molecules for High-Resolution Imaging and Analysis", ACS Nano, vol. 6, No. 9, Sep. 25, 2012 (Sep. 25, 2012), pp. 7928-7934.

Shuang Fang Lim, et al., "DNA methylation profiling in nanochannels", Biomicrofluidics, vol. 5, No. 3, Sep. 1, 2011 (Sep. 1, 2011), pp. 034106-1.

* cited by examiner

METHODS FOR PHRASING EPIGENETIC MODIFICATIONS OF GENOMES

CROSS-REFERENCE

This application claims the benefit of U.S. Provisional Patent Application No. 62/143,722, filed Apr. 6, 2015, which is incorporated herein by reference in its entirety.

BACKGROUND OF THE INVENTION

The Human Genome Project resulted in tremendous pay-offs for the biomedical community, including a remarkable reduction in sequencing costs, from $10 to less than $0.00001 per finished base. Exome sequencing is now routinely used in both research and clinical settings for the detection of inherited or acquired mutations related to disease, and the FDA has already listed over 100 drugs that have genotype information on their labels. In addition, the use of whole genome sequencing (WGS) is becoming more widespread. However, there are still major limitations of the current technology which severely limit the feasibility and utility of WGS for many studies.

SUMMARY OF THE INVENTION

In one aspect, provided herein is a method for analyzing epigenetic modification of a genome comprising: a. combing DNA from the genome on a surface; b. labeling the epigenetic modification with an affinity agent that binds to the modification; c. capturing the affinity agent and the DNA it binds; and d. preparing a sequencing library from the bound DNA with location specific oligonucleotide barcode.

In some cases, the affinity agent is an antibody. In some cases, the capturing comprises binding the antibody with a streptavidin. In some cases, the location specific oligonucleotide barcode is from a DNA microarray with spatially defined oligonucleotides. In some cases, the preparing comprises using in vitro transposition.

An aspect of the present disclosure provides a method for analyzing an epigenetic modification comprising: (a) stretching DNA comprising an epigenetic modification on a first surface; (b) labeling the epigenetic modification with an affinity agent that binds to the epigenetic modification; (c) capturing the DNA on a second surface by binding the affinity agent to the second surface, wherein the second surface comprises oligonucleotides, each oligonucleotide comprising a positional barcode sequence indicative of a location of the oligonucleotide on the second surface; and (d) preparing a sequencing library from the DNA, wherein a nucleic acid molecule of the sequencing library comprises (i) epigenetic information and (ii) positional barcode sequence information.

In some embodiments of aspects provided herein, the affinity agent comprises an antibody. In some embodiments of aspects provided herein, the affinity agent comprises biotin. In some embodiments of aspects provided herein, the capturing comprises binding the antibody with streptavidin. In some embodiments of aspects provided herein, the preparing the sequencing library comprises using in vitro transposition. In some embodiments of aspects provided herein, the positional barcode sequence is indicative of the location of the oligonucleotide on the second surface to within 2 μm. In some embodiments of aspects provided herein, the positional barcode sequence is indicative of the location of the oligonucleotide on the second surface to within 1 μm. In some embodiments of aspects provided herein, the positional barcode sequence is indicative of the location of the oligonucleotide on the second surface to within 0.5 μm. In some embodiments of aspects provided herein, the positional barcode sequence is indicative of the location of the oligonucleotide on the second surface to within 0.2 μm. In some embodiments of aspects provided herein, the positional barcode sequence is indicative of the location of the oligonucleotide on the second surface to within 0.1 μm. In some embodiments of aspects provided herein, the method further comprises sequencing the sequencing library to generate sequence reads, and assembling the sequence reads with the aid of the positional barcode sequence information. In some embodiments of aspects provided herein, the stretching DNA comprises combing. In some embodiments of aspects provided herein, the stretching DNA from the genome on the first surface results in the DNA being stretched on the first surface at a density of at least about 20 genomes per square centimeter. In some embodiments of aspects provided herein, the stretching DNA from the genome on the first surface results in the DNA being stretched on the first surface at a density of at least about 30× diploid genome coverage. In some embodiments of aspects provided herein, the first surface is hydrophobic. In some embodiments of aspects provided herein, the first surface comprises polylysine. In some embodiments of aspects provided herein, the DNA comprises genomic DNA. In some embodiments of aspects provided herein, the nucleic acid is at least 1 megabase (Mb) in length.

Another aspect of the present disclosure provides a kit for analyzing an epigenetic modification of a nucleic acid comprising: (a) an array substrate comprising oligonucleotides bound to the array substrate, each oligonucleotide comprising a positional barcode sequence indicative of a location of the oligonucleotide on the array substrate; and (b) an affinity agent that binds to the epigenetic modification of the nucleic acid.

In some embodiments of aspects provided herein, the affinity agent comprises an antibody. In some embodiments of aspects provided herein, the affinity agent comprises biotin. In some embodiments of aspects provided herein, the positional barcode sequence is indicative of the location of the oligonucleotide on the array substrate to within 2 μm. In some embodiments of aspects provided herein, the positional barcode sequence is indicative of the location of the oligonucleotide on the array substrate to within 1 μm. In some embodiments of aspects provided herein, the positional barcode sequence is indicative of the location of the oligonucleotide on the array substrate to within 0.5 μm. In some embodiments of aspects provided herein, the positional barcode sequence is indicative of the location of the oligonucleotide on the array substrate to within 0.2 μm. In some embodiments of aspects provided herein, the positional barcode sequence is indicative of the location of the oligonucleotide on the array substrate to within 0.1 μm.

Another aspect of the present disclosure provides a method for analyzing an epigenetic modification comprising: (a) assaying a nucleic acid for the presence of an epigenetic modification; and (b) determining a location of the epigenetic modification with reference to a solid support.

In some embodiments of aspects provided herein, the location of the epigenetic modification is determined with reference to the solid support to within 2 μm. In some embodiments of aspects provided herein, the location of the epigenetic modification is determined with reference to the solid support to within 1 μm. In some embodiments of aspects provided herein, the location of the epigenetic modification is determined with reference to the solid support to within 0.5 µm. In some embodiments of aspects provided herein, the location of the epigenetic modification is determined with reference to the solid support to within 0.2 µm. In some embodiments of aspects provided herein, the location of the epigenetic modification is determined with reference to the solid support to within 0.1 µm. In some embodiments of aspects provided herein, the method further comprises determining a location of at least two different epigenetic modifications of the nucleic acid with reference to a solid support. In some embodiments of aspects provided herein, the method further comprises determining a location of at least three different epigenetic modifications of the nucleic acid with reference to a solid support. In some embodiments of aspects provided herein, the method further comprises determining a location of at least four different epigenetic modifications of the nucleic acid with reference to a solid support. In some embodiments of aspects provided herein, the method further comprises determining a location of at least five different epigenetic modifications of the nucleic acid with reference to a solid support. In some embodiments of aspects provided herein, the nucleic acid comprises genomic DNA. In some embodiments of aspects provided herein, the nucleic acid is at least 1 megabase (Mb) in length. In some embodiments of aspects provided herein, the solid support comprises an oligonucleotide array.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
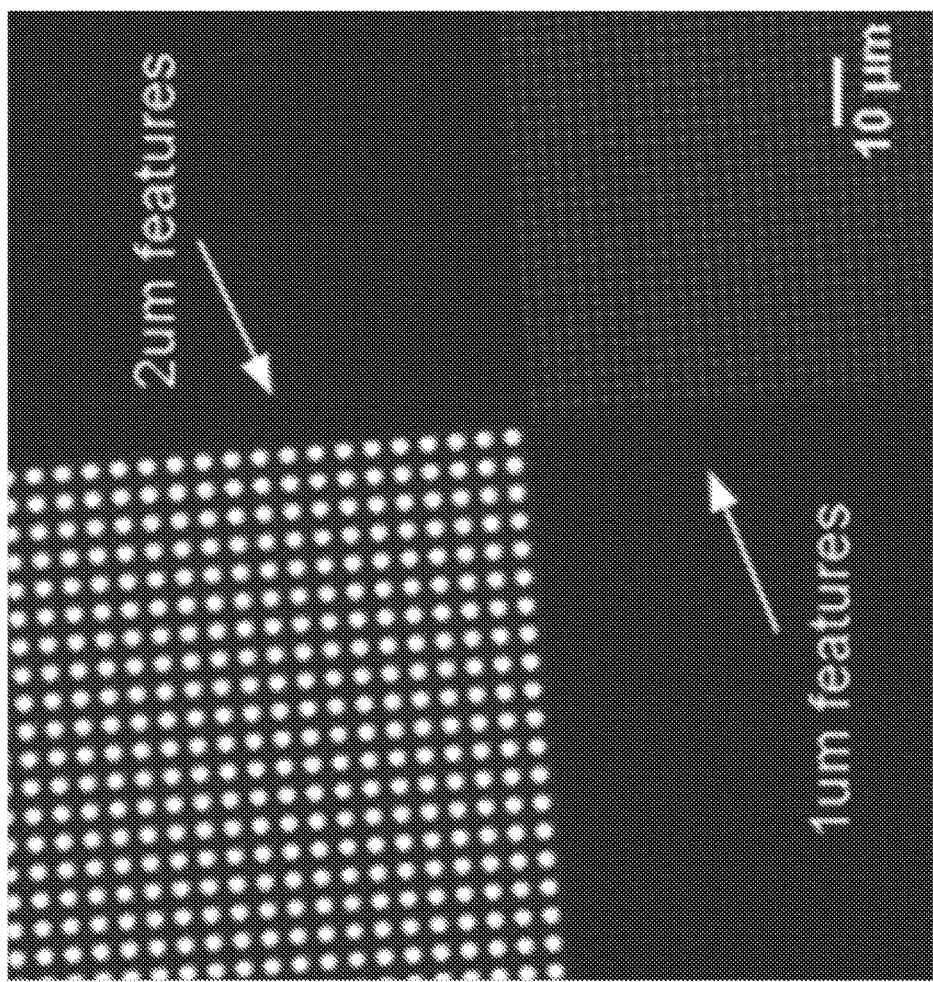
FIG. 1 illustrates a 20-mer oligo arrays synthesized with contact photolithography hybridized with complementary Cy3 labeled probes.

Reference will now be made in detail to the various embodiments of the invention, examples of which are illustrated in the accompanying drawings. While the invention will be described in conjunction with the various embodiments, it will be understood that they are not intended to limit the invention to those embodiments. On the contrary, the invention is intended to cover alternatives, modifications and equivalents, which may be included within the spirit and scope of the invention as defined by the appended claims.

This disclosure provides innovative technologies for analysis of the epigenome. These technologies can allow genome studies to accurately identify and phase epigenetic modifications. These technologies have extensive applications in molecular diagnostics, animal and plant breeding, and other fields. These technologies can decrease the cost of epigenetic analysis while dramatically increasing the accuracy and completeness of the results.

Techniques of the current disclosure can provide greater accuracy, greater precision, higher throughput, longer "reads," and the ability to decode more epigenetic modifications. Techniques of the present disclosure can be used to probe any epigenetic modification for which a specific binding agent (e.g., an antibody) can be generated.

This disclosure provides technologies to accurately identify epigenetic modifications on long single DNA molecules. The single molecule epigenetic measurements can allow for deciphering the connectivity of epigenetic modifications across megabase-scale individual DNA molecules, thus phasing the modifications and providing unprecedented details into the epigenetic state of the genome. The approach for solving this important challenge in epigenomics is very significant and can transform the way epigenetic modifications are studied.

Techniques of the present disclosure can involve stretching individual long DNA molecules (e.g., >1 MB) on a surface. The stretched DNA can be probed for epigenetic modifications, for example by using an antibody (e.g., 5-methylcytosine). The probe bound regions can be captured and the relative spatial position can be barcoded by using a DNA oligonucleotide chip. The barcoded and captured DNA molecules can serve as templates for sequencing, such as Next Generation Sequencing (NGS). The barcodes from the oligonucleotide chip can be used to identify the location on the chip from which the reads were generated, and thus provide a scaffold for assembling the short NGS reads (e.g., from an Illumina HiSeq) and resolving the epigenetic modifications. Scaffolding the short reads can help solve key problems in epigenomics by allowing for high quality assignments of the epigenetic modification to the genome phasing the modifications along megabase sized DNA molecules. One of skill in the art would appreciate that related reagents, instrumentation, and bioinformatics software can be prepared to facilitate epigenetic sequence analysis.

Techniques for preparing surfaces including oligonucleotide arrays with positional barcodes, preparing sequencing libraries, and other useful techniques are described in PCT Pub. No. WO/2015/085274, PCT Pub. No. WO/2015/085275, and PCT Pub. No. WO/2015/085268, each of which is incorporated by reference herein in its entirety.

Epigenetic modifications can be stable, heritable changes in the genome that affect the functional state of the genome, but not the nucleotide sequence. See, e.g., Feinberg, A. P. Phenotypic plasticity and the epigenetics of human disease, Nature 447, 433-440, (2007); Hammoud, S. S., Cairns, B. R. & Jones, D. A. Epigenetic regulation of colon cancer and intestinal stem cells, Current opinion in cell biology 25, 177-183, (2013); Feinberg, A. P. & Tycko, B. The history of cancer epigenetics, Nat Rev Cancer 4, 143-153, (2004); Calcagno, D. Q., Gigek, C. O., Chen, E. S., Burbano, R. R. & Smith Mde, A. DNA and histone methylation in gastric carcinogenesis, World journal of gastroenterology: WJG 19, 1182-1192, (2013); Gigek, C. O. et al. Epigenetic mechanisms in gastric cancer, Epigenomics 4, 279-294, (2012); Kilpinen, H. & Dermitzakis, E. T. Genetic and epigenetic contribution to complex traits, Human molecular genetics 21, R24-28, (2012); Jablonka, E. Epigenetic inheritance and plasticity: The responsive germline, Progress in biophysics and molecular biology 111, 99-107, (2013); all incorporated herein by reference.

The most widely studied epigenetic modification is 5-methylcytosine (5mC), which has a significant impact on the genome although most sequencing technologies are unable to recognize it. In addition to 5mC, there are many other epigenetic modifications that can alter gene expression and/or DNA repair pathways (e.g., 5-Hydroxymethylcytosine, 5-Formylcytosine, 5-Carboxylcytosine, 3-Methylcytosine). Epigenetic modifications can include covalent modifications of the deoxynucleotides, histone modifications, and regulatory noncoding RNAs, as well as noncovalent changes regulating nucleosome positioning. See, e.g., Calcagno, D. Q., Gigek, C. O., Chen, E. S., Burbano, R. R. & Smith Mde, A. DNA and histone methylation in gastric carcinogenesis, World journal of gastroenterology: WJG 19, 1182-1192, (2013); Calo, E. & Wysocka, J. Modification of enhancer chromatin: what, how, and why?, Molecular cell 49, 825-837, (2013); Cantarino, N., Douet, J. & Buschbeck, M. MacroH2A—An epigenetic regulator of cancer, Cancer letters, (2013); Pirooznia, S. K. & Elefant, F. Targeting specific HATs for neurodegenerative disease treatment: translating basic biology to therapeutic possibilities, Front Cell Neurosci 7, 30, (2013); Sharma, N. L., Groselj, B., Hamdy, F. C. & Kiltie, A. E. The emerging role of histone deacetylase (HDAC) inhibitors in urological cancers, BJU Int 111, 537-542, (2013); Yang, Y. A. & Yu, J. EZH2, an epigenetic driver of prostate cancer, Protein Cell 4, 331-341, (2013); Salomoni, P. The PML-Interacting Protein DAXX: Histone Loading Gets into the Picture, Front Oncol 3, 152, (2013); Zoldos, V., Novokmet, M., Beceheli, I. & Lauc, G. Genomics and epigenomics of the human glycome, Glycoconj J 30, 41-50, (2013); Song, C. X. et al. Sensitive and specific single-molecule sequencing of 5-hydroxymethylcytosine, Nature methods 9, 75-77, (2012); Clark, T. A., Spittle, K. E., Turner, S. W. & Korlach, J. Direct detection and sequencing of damaged DNA bases, Genome Integr 2, 10, (2011); Murray, I. A. et al. The methylomes of six bacteria, Nucleic acids research 40, 11450-11462, (2012); Fang, G. et al. Genome-wide mapping of methylated adenine residues in pathogenic *Escherichia coli* using single-molecule real-time sequencing, Nature biotechnology 30, 1232-1239, (2012); all incorporated herein by reference.

Understanding the epigenome is an important component to understanding many aspects of cell biology and physiology. Furthermore, some DNA modifications (either epigenetic or DNA damage) are involved in diseases, such as cancer. See, e.g., Baer, C., Claus, R. & Plass, C. Genome-wide epigenetic regulation of miRNAs in cancer, Cancer research 73, 473-477, (2013); He, S., Liu, Z., Oh, D. Y. & Thiele, C. J. MYCN and the epigenome, Front Oncol 3, 1, (2013); Juergens, R. A. & Rudin, C. M. Aberrant epigenetic regulation, Am Soc Clin Oncol Educ Book 2013, 295-300, (2013); Ma, X., Wang, Y. W., Zhang, M. Q. & Gazdar, A. F. DNA methylation data analysis and its application to cancer research, Epigenomics 5, 301-316, (2013); Verma, M. Cancer control and prevention: nutrition and epigenetics, Curr Opin Clin Nutr Metab Care 16, 376-384, (2013), all incorporated herein by reference. Some DNA modifications (either epigenetic or DNA damage) are involved in diseases, such as neurological functions and mental health. See, e.g., McQuown, S. C. & Wood, M. A. Epigenetic regulation in substance use disorders, Curr Psychiatry Rep 12, 145-153, (2010); Adwan, L. & Zawia, N. H. Epigenetics: A novel therapeutic approach for the treatment of Alzheimer's disease, Pharmacology & therapeutics 139, 41-50, (2013); Ptak, C. & Petronis, A. Epigenetic approaches to psychiatric disorders, Dialogues Clin Neurosci 12, 25-35, (2010); Kofink, D., Boks, M. P., Timmers, H. T. & Kas, M. J. Epigenetic dynamics in psychiatric disorders: Environmental programming of neurodevelopmental processes, Neurosci Biobehav Rev 37, 831-845, (2013); LaPlant, Q. & Nestler, E. J. CRACKing the histone code: cocaine's effects on chromatin structure and function, Horm Behav 59, 321-330, (2011); Maze, I. & Nestler, E. J. The epigenetic landscape of addiction. Annals of the New York Academy of Sciences 1216, 99-113, (2011); Nielsen, D. A., Utrankar, A., Reyes, J. A., Simons, D. D. & Kosten, T. R. Epigenetics of drug abuse: predisposition or response, Pharmacogenomics 13, 1149-1160, (2012); Madsen, H. B., Brown, R. M. & Lawrence, A. J. Neuroplasticity in addiction: cellular and transcriptional perspectives, Front Mol Neurosci 5, 99, (2012); McCarthy, D. M., Brown, A. N. & Bhide, P. G. Regulation of BDNF expression by cocaine, Yale J Biol Med 85, 437-446, (2012); Schmidt, H. D., McGinty, J. F., West, A. E. & Sadri-Vakili, G. Epigenetics and psychostimulant addiction, Cold Spring Harb Perspect Med 3, a012047, (2013); Nestler, E. J. Transcriptional mechanisms of drug addiction, Clin Psychopharmacol Neurosci 10, 136-143, (2012); all incorporated herein by reference.

For example, understanding the impact of epigenetic modifications on the genome may help explain the incomplete penetrance observed in neurological conditions such as schizophrenia and other inherited diseases. See, e.g., Archer, T., Beninger, R. J., Palomo, T. & Kostrzewa, R. M. Epigenetics and biomarkers in the staging of neuropsychiatric disorders, Neurotox Res 18, 347-366, (2010); Van Winkel, R. et al. REVIEW: Genome-wide findings in schizophrenia and the role of gene-environment interplay, CNS Neurosci Ther 16, e185-192, (2010); Brown, A. S. The environment and susceptibility to schizophrenia, Prog Neurobiol 93, 23-58, (2011); Molfese, D. L. Advancing neuroscience through epigenetics: molecular mechanisms of learning and memory, Dev Neuropsychol 36, 810-827, (2011); Thibaut, F. Why schizophrenia genetics needs epigenetics: a review, Psychiatr Danub 24, 25-27, (2012); Gebicke-Haerter, P. J. Epigenetics of schizophrenia. Pharmacopsychiatry 45 Suppl 1, S42-48, (2012); Eren Kocak, E. & Ertugrul, A. Psychiatric disorders and epigenetics, Turk Psikiyatri Derg 23, 130-140, (2012); Svrakic, D. M., Zorumski, C. F., Svrakic, N. M., Zwir, I. & Cloninger, C. R. Risk architecture of schizophrenia: the role of epigenetics, Curr Opin Psychiatry 26, 188-195, (2013); all incorporated herein by reference.

The epigenome sequencing technologies disclosed herein can help transform our understanding of the genetic and epigenetic basis of complex diseases, and this technology can facilitate the discovery of regulatory mechanisms and biomarkers for cellular development, differentiation, and disease.

DNA Damage.

Many DNA modifications are the direct result of a DNA damaging agent. Techniques disclosed herein can be used to detect these modifications, in addition to the standard epigenetic modifications such as 5-methylcytosine. DNA damage is known to play a critical role in many diseases, so developing sequencing technologies capable of detecting damaged bases is important to improving understanding, detection, and treatment of these diseases (see, e.g., Korlach, J. & Turner, S. W. Going beyond five bases in DNA sequencing, Curr Opin Struct Biol 22, 251-261, (2012); Preston, B. D., Albertson, T. M. & Herr, A. J. DNA replication fidelity and cancer, Seminars in cancer biology 20, 281-293, (2010), all incorporated herein by reference). For example, oxidative damage of the mitochondrial genome is related to aging and neurodegenerative diseases (see, e.g., Lindahl, T. Instability and decay of the primary structure of DNA, Nature 362, 709-715, (1993); Beal, M. F. Mitochondria take center stage in aging and neurodegeneration, Ann Neurol 58, 495-505, (2005); Maynard, S., Schurman, S. H., Harboe, C., de Souza-Pinto, N. C. & Bohr, V. A. Base excision repair of oxidative DNA damage and association with cancer and aging, Carcinogenesis 30, 2-10, (2009); De Bont, R. & van Larebeke, N. Endogenous DNA damage in humans: a review of quantitative data, Mutagenesis 19, 169-185, (2004); all incorporated herein by reference). Environmental factors, such as UV exposure, smoking, and aging related depurination can also damage DNA (see, e.g., Laird, P. W. & Jaenisch, R. DNA methylation and cancer, Human molecular genetics 3 Spec No, 1487-1495, (1994); De Bont, R. & van Larebeke, N. Endogenous DNA damage in humans: a review of quantitative data, Mutagenesis 19, 169-185, (2004); all incorporated herein by reference). Furthermore, DNA polymerases can mis-incorporate an RNA base (instead of a DNA base), which can contribute to genome instability and cancer (see, e.g., Nick McElhinny, S. A. et al. Abundant ribonucleotide incorporation into DNA by yeast replicative polymerases, Proceedings of the National Academy of Sciences of the United States of America 107, 4949-4954, (2010); Nick McElhinny, S. A. et al. Genome instability due to ribonucleotide incorporation into DNA, Nat Chem Biol 6, 774-781, (2010); all incorporated herein by reference).

Limitations of Existing Technologies.

DNA sequencing technologies have revolutionized genetic research and are beginning to have a significant impact on human health care. However, there are major shortcomings of next generation sequencing. Identifying epigenetic modifications is not straightforward and current technologies capable of measuring epigenetic modifications are limited. Of the many epigenetic modifications that have been discovered, only 5mC can be identified using bisulfite sequencing. Studying the remaining modifications is difficult or impossible on a genomic scale (see, e.g., Korlach, J. & Turner, S. W. Going beyond five bases in DNA sequencing. Curr Opin Struct Biol 22, 251-261, (2012), incorporated herein by reference).

Pacific Biosciences Single Molecule Sequencing.

Pacific Biosciences (PacBio) sequencing is currently the only available method that can directly sequence epigenetic modifications. It has been used to detect several bacterial (5-methylcytosine, 4-methylcytosine and 6-methyladenine) and eukaryotic (5-methylcytosine, 6-methyladenine, 5-hydroxymethylcytosine) epigenetic modifications (see, e.g., Clark, T. A. et al. Characterization of DNA methyltransferase specificities using single-molecule, real-time DNA sequencing, Nucleic acids research 40, e29, (2012); Flusberg, B. A. et al. Direct detection of DNA methylation during single-molecule, real-time sequencing, Nature methods 7, 461-465, (2010); all incorporated herein by reference). Additionally, it has been further applied to characterize the kinetic signatures of nucleotide incorporation using synthetic templates with DNA damage modifications (see, e.g., Clark, T. A., Spittle, K. E., Turner, S. W. & Korlach, J. Direct detection and sequencing of damaged DNA bases, Genome Integr 2, 10, (2011), incorporated herein by reference). However, PacBio is limited to detecting epigenetic modifications that alter the nucleotide incorporation rate in a unique and predictable manner. For example, several modifications have similar signatures (e.g., typical 6-methyl adenine modification vs. 1-methyl adenine characteristic of DNA damage), and thus in order to accurately determine which bases are modified, a minimum coverage of 50-250× coverage can be required (see, e.g., Korlach, J. & Turner, S. W. Going beyond five bases in DNA sequencing, Curr Opin Struct Biol 22, 251-261, (2012), incorporated herein by reference), which significantly reduces the already low throughput of the PacBio system. Furthermore, the throughput and cost of PacBio sequencing can prevent it from being a realistic approach for true epigenome sequencing. By comparison, techniques of the current disclosure can provide greater accuracy, higher throughput, longer "reads," and the ability to decode more epigenetic modifications.

Long Stretched Single Molecule Epigenetic Mapping.

Current optical mapping techniques utilized by companies such as OpGen and BioNano Genomics can also probe for epigenetic modifications, but they are severely limited. First, the other approaches are not able to generate the resolution that we can achieve, and secondly they are limited to primarily 5-methylcytosine and therefore miss important information (Ananiev, G. E. et al. Optical mapping discerns genome wide DNA methylation profiles. BMC molecular biology 9, 68, (2008); Levy-Sakin, M. et al. Toward single-molecule optical mapping of the epigenome. ACS Nano 8, 14-26, (2014), all incorporated herein by reference). Our technology will be capable of probing any epigenetic modification for which a specific antibody can be generated, and the position can be determined with extraordinary precision.

In an age of ever decreasing sequencing costs, new genomes are being released at an unprecedented rate. Existing technologies, however, are unable to capture the full breadth of information present in the genome, and genome-wide epigenetic modification "sequencing" cannot currently be performed. Techniques of the present disclosure can be used to provide complete maps of the epigenome, encompassing DNA modifications (e.g., all possible known DNA modifications for which antibodies or other probes can be generated) across entire chromosomes. This information is critical for research into genetically linked diseases, cancer, the aging process, the impact of environmental conditions on the epigenome, and inheritance and evolution as a whole.

The methods, compositions, kits, and techniques of the invention integrate several highly innovative and breakthrough technologies in order to address the major limitation of current next generation sequencing analysis of the epigenome. Techniques of the present disclosure can provide complete epigenome sequencing of any modification for which an antibody or an affinity binding agent can be developed.

The technology disclosed herein can provide phased maps of the epigenomic modifications across long stretches of DNA, and ultimately entire chromosomes, enabling new measurements and studies not previously possible.

Techniques of the present disclosure can capture and immobilize long genomic DNA regions and selectively sequence regions with epigenetic modifications. The epigenetic modifications can be within the short sequence reads obtained. The immobilized genomic DNA can provide a megabase scaffold from which to hang the short reads, thereby localizing and phasing epigenetic modifications on single molecules across long genomic DNA regions. The basic approach can involve stretching many individual DNA molecules on a surface (e.g., 30-40× diploid genome coverage). The ends of the long DNA molecules can be captured and a spatially localized library can be constructed. The sequence between the ends can be probed for epigenetic modifications (e.g., 5-methylcytosine) and sequencing libraries can also be constructed for genome regions that contain epigenetic modifications. The libraries can be prepared on a spatially barcoded chip so their relative location in the genome can be determined. The NGS library can then be sequenced using any NGS platform (e.g., Illumina HiSeq). Since the primers used to generate the sequencing library are barcoded, a scaffold for assembling the short NGS reads and identifying the location of the epigenetic modifications can be obtained.

Cell Lines and DNA Samples

A variety of DNA samples can be used. It is preferred to use long DNA that has not been manipulated extensively. In some cases, cell lysate containing chromosomal DNA can be used for DNA combing and subsequent epigenetic analysis based upon the current method.

A "nucleic acid molecule" or "nucleic acid" as referred to herein can be deoxyribonucleic acid (DNA) or ribonucleic acid (RNA) including known analogs or a combination thereof unless otherwise indicated. Nucleic acid molecules to be sequenced herein can be obtained from any source of nucleic acid. The nucleic acid molecule can be single-stranded or double-stranded. In some cases, the nucleic acid molecule is DNA. The DNA can be obtained and purified using standard techniques in the art and include DNA in purified or unpurified form. The DNA can be mitochondrial DNA, cell-free DNA, complementary DNA (cDNA), or genomic DNA. In some cases, the nucleic acid molecule is genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can derived from one or more of chromosome 1, 2, 3, 4, 5, 6, 7, 8, 9, 10, 11, 12, 13, 14, 15, 16, 17, 18, 19, 20, 21, 22, X, or Y. The RNA can be obtained and purified using standard techniques in the art and include RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long nc RNAs.

The source of nucleic acid for use in the methods and compositions described herein can be a sample comprising the nucleic acid. The nucleic acid can be isolated from the sample and purified by any of the methods known in the art for purifying the nucleic acid from the sample. The sample can be derived from a non-cellular entity comprising polynucleotides (e.g., a virus) or from a cell-based organism (e.g., member of archaea, bacteria, or eukarya domains). In some cases, the sample is obtained from a swab of a surface, such as a door or bench top.

The sample can be from a subject, e.g., a plant, fungi, eubacteria, archeabacteria, protest, or animal. The subject can be an organism, either a single-celled or multi-cellular organism. The subject can be cultured cells, which can be primary cells or cells from an established cell line, among others. The sample can be isolated initially from a multi-cellular organism in any suitable form. The animal can be a fish, e.g., a zebrafish. The animal can be a mammal. The mammal can be, e.g., a dog, cat, horse, cow, mouse, rat, or pig. The mammal can be a primate, e.g., a human, chimpanzee, orangutan, or gorilla. The human can be a male or female. The sample can be from a human embryo or human fetus. The human can be an infant, child, teenager, adult, or elderly person. The female can be pregnant, suspected of being pregnant, or planning to become pregnant. In some cases, the sample is a single or individual cell from a subject and the polynucleotides are derived from the single or individual cell. In some cases, the sample is an individual micro-organism, or a population of micro-organisms, or a mixture of micro-organisms and host cellular or cell free nucleic acids.

The sample can be from a subject (e.g., human subject) who is healthy. In some cases, the sample is taken from a subject (e.g., an expectant mother) at at least 4, 5, 6, 7, 8, 9, 10, 11, 12, 13, 14, 15, 16, 17, 18, 19, 20, 21, 22, 23, 24, 25, or 26 weeks of gestation. In some cases, the subject is affected by a genetic disease, a carrier for a genetic disease or at risk for developing or passing down a genetic disease, where a genetic disease is any disease that can be linked to a genetic variation such as mutations, insertions, additions, deletions, translocation, point mutation, trinucleotide repeat disorders and/or single nucleotide polymorphisms (SNPs).

The sample can be from a subject who has a specific disease, disorder, or condition, or is suspected of having (or at risk of having) a specific disease, disorder or condition. For example, the sample can be from a cancer patient, a patient suspected of having cancer, or a patient at risk of having cancer. The cancer can be, e.g., acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chromic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom Macroglobulinemia, or Wilms Tumor. The sample can be from the cancer and/or normal tissue from the cancer patient.

The sample can be aqueous humour, vitreous humour, bile, whole blood, blood serum, blood plasma, breast milk, cerebrospinal fluid, cerumen, enolymph, perilymph, gastric juice, mucus, peritoneal fluid, saliva, sebum, semen, sweat, tears, vaginal secretion, vomit, feces, or urine. The sample can be obtained from a hospital, laboratory, clinical or medical laboratory. The sample can be taken from a subject.

The sample can be an environmental sample comprising medium such as water, soil, air, and the like. The sample can be a forensic sample (e.g., hair, blood, semen, saliva, etc.). The sample can comprise an agent used in a bioterrorist attack (e.g., influenza, anthrax, smallpox).

The sample can comprise nucleic acid. The sample can comprise cell-free nucleic acid. The sample can be a cell line, genomic DNA, cell-free plasma, formalin fixed paraffin embedded (FFPE) sample, or flash frozen sample. A formalin fixed paraffin embedded sample can be deparaffinized before nucleic acid is extracted. The sample can be from an organ, e.g., heart, skin, liver, lung, breast, stomach, pancreas, bladder, colon, gall bladder, brain, etc. Nucleic acids can be extracted from a sample by means available to one of ordinary skill in the art.

The sample can be processed to render it competent for fragmentation, ligation, denaturation, amplification, stretching, and/or sequencing or any of the methods provided herein. Exemplary sample processing can include lysing cells of the sample to release nucleic acid, purifying the sample (e.g., to isolate nucleic acid from other sample components, which can inhibit enzymatic reactions), diluting/concentrating the sample, and/or combining the sample with reagents for further nucleic acid processing. In some examples, the sample can be combined with a restriction enzyme, reverse transcriptase, or any other enzyme of nucleic acid processing.

A "nucleic acid molecule" or "nucleic acid" as referred to herein can be an "oligonucleotide" "aptamer" or a "polynucleotide". The term "oligonucleotide" can refer to a nucleotide chain, typically less than 200 residues long, e.g., between 15 and 100 nucleotides long. The oligonucleotide can comprise at least or about 1, 2, 3, 4, 5, 6, 7, 8, 9, 10, 15, 20, 25, 30, 35, 40, 45, or 50 bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligo (e.g., primer). In some cases, the oligos are 5'-acrydite-modified oligos. The oligos can be coupled to the polymer coatings as provided herein on surfaces as provided herein. The oligonucleotides can comprise cleavable linkages. Cleavable linkages can be enzymatically cleavable. Oligonucleotides can be single- or double-stranded. The terms "primer" and "oligonucleotide primer" can refer to an oligonucleotide capable of hybridizing to a complementary nucleotide sequence. The term "oligonucleotide" can be used interchangeably with the terms "primer," "adapter," and "probe." The term "polynucleotide" can refer to a nucleotide chain typically greater than 200 residues long. Polynucleotides can be single- or double-stranded.

The term "hybridization"/"hybridizing" and "annealing" can be used interchangeably and can refer to the pairing of complementary nucleic acids.

Chip Design and DNA Barcodes

To resolve the location of the epigenetic modifications, a set of barcodes which uniquely define the oligonucleotide position on the chip can be provided. The barcodes can be accurately sequenced (e.g., GC content between 40% and 60%, no homopolymer runs longer than two, no self-complimentary stretches longer than 3, not present in human genome reference). Most importantly, to error-proof spatial addressability, each barcode preferably has at least four edit distance apart; that is, each barcode is at least four deletions, insertions, or substitutions away from any other barcode in the array. For example, a set of about 1.5 million 18-base barcodes can be employed.

The term "barcode" can refer to a known nucleic acid sequence that allows some feature of a nucleic acid (e.g., oligo) with which the barcode is associated to be identified. In some cases, the feature of the nucleic acid to be identified is the spatial position of each nucleic acid (e.g., oligo) on an array or chip. The barcodes can be designed for precision sequence performance, e.g., GC content between 40% and 60%, no homo-polymer runs longer than two, no self-complementary stretches longer than 3, and be comprised of sequences not present in a human genome reference. A barcode sequence can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. A barcode sequence can be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. A barcode sequence can be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. An oligonucleotide (e.g., primer or adapter) can comprise about, more than, less than, or at least 1, 2, 3, 4, 5, 6, 7, 8, 9, or 10 different barcodes. Barcodes can be of sufficient length and comprise sequences that can be sufficiently different to allow the identification of the spatial position of each nucleic acid (e.g., oligo) based on barcode(s) with which each nucleic acid is associated. In some cases, each barcode is, for example, four deletions or insertions or substitutions away from any other barcode in an array. The oligos in each array spot on the barcoded oligo array can comprise the same barcode sequence and oligos in different array spots can comprise different barcode sequences. The barcode sequence used in one array spot can be different from the barcode sequence in any other array spot. Alternatively, the barcode sequence used in one array spot can be the same as the barcode sequence used in another array spot, as long as the two array spots are not adjacent. Barcode sequences corresponding to particular array spots can be known from the controlled synthesis of the array. Alternatively, barcode sequences corresponding to particular array spots can be known by retrieving and sequencing material from particular array spots. A candidate set of barcodes containing 1.5 million 18 base barcodes was designed as an example.

Array Surface Preparation

The methods and compositions provided in this disclosure can comprise preparing a surface for generating an array. In some cases, the array is an array of oligonucleotides (oligonucleotide array or oligo array). The preparation of the surface can comprise creating a polymer coating on the surface. The surface can comprise glass, silica, titanium oxide, aluminum oxide, indium tin oxide (ITO), silicon, polydimethylsiloxane (PDMS), polystyrene, polycyclicolefins, polymethylmethacrylate (PMMA), cyclic olefin copolymer (COC), other plastics, titanium, gold, other metals, or other suitable materials. The surface can be flat or round, continuous or non-continuous, smooth or rough. Examples of surfaces include flow cells, sequencing flow cells, flow channels, microfluidic channels, capillary tubes, piezoelectric surfaces, wells, microwells, microwell arrays, microarrays, chips, wafers, non-magnetic beads, magnetic beads, ferromagnetic beads, paramagnetic beads, superparamagnetic beads, and polymer gels.

In some cases, preparation of surfaces as described herein for the generation of oligonucleotide arrays as provided herein comprises bonding initiator species to the surface. In some cases, the initiator species comprises at least one organosilane. In some cases, the initiator species comprises one or more surface bonding groups. In some cases, the initiator species comprises at least one organosilane and the at least one organosilane comprises one or more surface bonding groups. The organosilane can comprise one surface-bonding group, resulting in a mono-pedal structure. The organosilane can comprise two surface-bonding groups, resulting in a bi-pedal structure. The organosilane can comprise three surface-bonding groups, resulting in a tri-pedal structure. The surface bonding group can comprise MeO$_3$Si, (MeO)$_3$Si, (EtO)$_3$Si, (AcO)$_3$Si, (Me$_2$N)$_3$Si, and/or (HO)$_3$Si. In some cases, the surface bonding group comprises MeO$_3$Si. In some cases, the surface bonding group comprises (MeO)$_3$Si. In some cases, the surface bonding group comprises (EtO)$_3$Si. In some cases, the surface bonding group comprises (AcO)$_3$Si. In some cases, the surface bonding group comprises (Me$_2$N)$_3$Si. In some cases, the surface bonding group comprises (HO)$_3$Si. In some cases, the organosilane comprises multiple surface bonding groups. The multiple surface bonding groups can be the same or can be different. In some cases, the initiator species comprises at least one organophosphonic acid, wherein the surface bonding group comprises (HO)$_2$P(=O). The organophosphonic acid can comprise one surface-bonding group, resulting in a mono-pedal structure. The organophosphonic acid can comprise two surface-bonding groups, resulting in a bi-pedal structure. The organophosphonic acid can comprise three surface-bonding groups, resulting in a tri-pedal structure.

In some cases, a surface as provided herein comprises a surface-bound initiator species as provided herein for the generation of oligo arrays comprises a surface coating or functionalization. The surface coating or functionalization can be hydrophobic or hydrophilic. The surface coating can comprise a polymer coating or polymer brush, such as polyacrylamide or modified polyacrylamide. The surface coating can comprise a gel, such as a polyacrylamide gel or modified polyacrylamide gel. The surface coating can comprise metal, such as patterned electrodes or circuitry. The surface coating or functionalization can comprise a binding agent, such as streptavidin, avidin, antibodies, antibody fragments, or aptamers. The surface coating or functionalization can comprise multiple elements, for example a polymer or gel coating and a binding agent. In some cases, preparation of surfaces as described herein for the generation of oligonucleotide arrays as provided herein comprises forming a polymer coating on the surface-bound initiator species. The surface bound initiator species can be any surface bound initiator species known in the art. In some cases, the surface bound initiator species comprises an organosilane as provided herein. The organosilane can comprise one or more surface bonding groups as described herein. In some cases, the organosilane comprises at least two surface bonding groups. The presence of two or more surface bonding groups can serve to increase the stability of an initiator species-polymer coating complex. The one or more surface bonding groups can be any surface bonding group as provided herein. The resulting polymer coatings can comprise linear chains. The resulting polymer coatings can comprise chains that are branched. The branched chains can be lightly branched. A lightly branched chain can comprise less than or about 1, 2, 3, 4, 5, 6, 7, 8, 9, or 10 branches. The polymer coatings can form polymer brush thin-films. The polymer coatings can include some cross-linking. The polymer coatings can form a graft structure. The polymer coatings can form a network structure. The polymer coatings can form a branched structure. The polymers can comprise homogenous polymers. The polymers can comprise block copolymers. The polymers can comprise gradient copolymers. The polymers can comprise periodic copolymers. The polymers can comprise statistical copolymers.

In some cases, the polymer coating formed on the surface bound initiator species comprises polyacrylamide (PA). The polymer can comprise polymethylmethacrylate (PMMA). The polymer can comprise polystyrene (PS). The polymer can comprise polyethylene glycol (PEG). The polymer can comprise polyacrylonitrile (PAN). The polymer can comprise poly(styrene-r-acrylonitrile) (PSAN). The polymer can comprise a single type of polymer. The polymer can comprise multiple types of polymer. The polymer can comprise polymers as described in Ayres, N. (2010). Polymer brushes: Applications in biomaterials and nanotechnology *Polymer Chemistry*, 1(6), 769-777, or polymers as described in Barbey, R., Lavanant, L., Paripovic, D., Schuwer, N., Sugnaux, C., Tugulu, S., & Klok, H. A. (2009) Polymer brushes via surface-initiated controlled radical polymerization: synthesis, characterization, properties, and applications. *Chemical reviews*, 109(11), 5437-5527, the disclosure of each of which is herein incorporated by reference in its entirety.

Polymerization of the polymer coating on the surface bound initiator species can comprise methods to control polymer chain length, coating uniformity, or other properties. The polymerization can comprise controlled radical polymerization (CRP), atom-transfer radical polymerization (ATRP), or reversible addition fragmentation chain-transfer (RAFT). The polymerization can comprise living polymerization processes as described in Ayres, N. (2010). Polymer brushes: Applications in biomaterials and nanotechnology *Polymer Chemistry*, 1(6), 769-777, or as described in Barbey, R., Lavanant, L., Paripovic, D., Schiuwer, N., Sugnaux, C., Tugulu, S., & Klok, H. A. (2009) Polymer brushes via surface-initiated controlled radical polymerization: synthesis, characterization, properties, and applications. *Chemical reviews*, 109(11), 5437-5527, the disclosure of each of which is herein incorporated by reference in its entirety.

The polymer coating formed on a surface bound initiator species as provided herein can be of uniform thickness over the entire area of the polymer coating. The polymer coating formed on a surface bound initiator species as provided herein can be of varying thickness across the area of the polymer coating. The polymer coating can be at least 1 µm, 2 µm, 3 µm, 4 µm, 5 µm, 7 µm, 8 µm, 9 µm, 10 µm, 15 µm, 20 µm, 25 µm, 30 µm, 40 µm thick. The polymer coating may be at least 50 µm thick. The polymer coating may be at least 75 µm thick. The polymer coating may be at least 100 µm thick. The polymer coating may be at least 150 µm thick. The polymer coating may be at least 200 µm thick. The polymer coating may be at least 300 µm thick. The polymer coating may be at least 400 µm thick. The polymer coating may be at least 500 µm thick. The polymer coating may be between about 1 µm and about 10 µm thick. The polymer coating may be between about 5 µm and about 15 µm thick. The polymer coating may be between about 10 µm and about 20 µm thick. The polymer coating may be between about 30 µm and about 50 µm thick. The polymer coating may be between about 10 µm and about 50 µm thick. The polymer coating may be between about 10 µm and about 100 µm thick. The polymer coating may be between about 50 µm and about 100 µm thick. The polymer coating may be between about 50 µm and about 200 µm thick. The polymer coating may be between about 100 µm and about 30 µm thick. The polymer coating may be between about 100 µm and about 500 µm thick.

In some cases, physiochemical properties of the polymer coatings herein are modified. The modification can be achieved by incorporating modified acrylamide monomers during the polymerization process. In some cases, ethoxylated acrylamide monomers are incorporated during the polymerization process. The ethoxylated acrylamide monomers can comprise monomers of the form $CH_2=CH-CO-NH(-CH_2-CH_2-O-)_nH$. The ethoxylated acrylamide monomers can comprise hydroxyethyl acrylamide monomers. The ethoxylated acrylamide monomers can comprise ethylene glycol acrylamide monomers. The ethoxylated acrylamide monomers can comprise hydroxyethylmethacrylate (HEMA). The incorporation of ethoxylated acrylamide monomers can result in a more hydrophobic polyacrylamide surface coating. In some cases, phosphorylcholine acrylamide monomers are incorporated during the polymerization process. In some cases, betaine acrylamide monomers are incorporated during the polymerization process.

The surfaces used for the transfer methods as provided herein (e.g., template surface and/or the recipient surface) can comprise a range of possible materials. In some cases, the surface comprises a polymer gel on a substrate, such as a polyacrylamide gel or a PDMS gel. In some cases, the surface comprises a gel without a substrate support. In some cases, the surface comprises a thin coating on a substrate, such as sub-200 nm coatings of polymer. In some cases, the surface comprises an uncoated substrate, such as glass or silicon.

The coatings and/or gels can have a range of thicknesses or widths. The gel or coating can have a thickness or width of about 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of less than 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of more than 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of at least 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of at most 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of between 0.0001 and 200 mm, between 0.01 and 20 mm, between 0.1 and 2 mm, or between 1 and 10 mm. The gel or coating can have a thickness or width of from about 0.0001 to about 200 mm, about 0.01 to about 20 mm, about 0.1 to about 2 mm, or about 1 to about 10 mm. In some cases, the gel or coatings comprises a width or thickness of about 10 microns.

Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, and/or betaine acrylamide monomers.

Gels and coatings can additionally comprise markers or reactive sites to allow incorporation of markers. Markers can comprise oligonucleotides. For example, 5'-acrydite-modified oligonucleotides can be added during the polymerization process of a polyacrylamide gel or coating. Reactive sites for incorporation of markers can comprise bromoacetyl sites, azides, sites compatible with azide-alkyne Huisgen cycloaddition, or other reactive sites. Markers can be incorporated into the polymer coatings in a controlled manner, with particular markers located at particular regions of the polymer coatings. Markers can be incorporated into the polymer coatings at random, whereby particular markers can be randomly distributed throughout the polymer coatings.

In some cases, a surface with a gel coating can be prepared as follows: glass slides are cleaned (e.g., with NanoStrip solution), rinsed (e.g. with DI water), and dried (e.g. with $N_2$); the glass slide surface is functionalized with acrylamide monomers; a silanation solution is prepared (e.g., 5% by volume (3-acrylamidopropyl)trimethoxysilane in ethanol and water); the glass slide is submerged in the silanation solution (e.g. for 5 hours at room temperature), rinsed (e.g., with DI water), and dried (e.g. with $N_2$); a 12% acrylamide gel mix is prepared (e.g., 5 mL $H_2O$, 1 mg gelatin, 600 mg acrylamide, 32 mg bis-acrylamide); a 6% acrylamide gel mix is prepared (e.g., 50 µL 12% acrylamide gel mix, 45 µL DI water, 5 µL 5'-acrydite modified oligonucleotide primers (1 mM, vortexed to mix); 6% acrylamide gel mix is activated (e.g., 1.3 µL of 5% ammonium persulfate and 1.3 µL of 5% TEMED are each added per 100 µL of gel mix and vortexed); gel mix is applied to a surface (e.g. silanized functionalized glass slide surface), evenly spread (e.g. by pressing with a cover slip or by spin coating), and allowed to polymerize (e.g., 20 minutes at room temperature).

Photo-Directed Synthesis of the DNA Barcode Array

High-density oligonucleotide arrays of probe lengths up to 60 bp are commercially available, such as from Affymetrix, NimbleGen, and Agilent. With conventional contact lithography, stepwise misalignment can limit the achievable minimum feature size to about 1 to 2 µm, as demonstrated by the 20-mer oligo array synthesized using photolytic protecting group chemistry (see, e.g., FIG. 1). Reduction of the feature size below 1 µm can be achieved through the combined use of projection lithography and contrast enhancing photoacid generating polymer films. Established steppers (e.g., ASML PAS5500) routinely print 5× reduced patterns in the sub-micron range with ±0.060 µm placement accuracy. In addition, the fully synthesized sequence can be ~60 bases (~20 base barcode, flanked by two ~20 base universal adaptors). The top adaptor can eventually prime the immobilized DNA as discussed herein, while the bottom adaptor can serve as the first adaptor for NGS library preparation.

The feature size of arrays synthesized by techniques disclosed herein can be less than about 10 µm, 9 µm, 8 µm, 7 µm, 6 µm, 5 µm, 4 µm, 3 µm, 2 µm, 1 µm, 0.9 µm, 0.8 µm, 0.7 µm, 0.6 µm, 0.5 µm, 0.4 µm, 0.3 µm, 0.2 µm, or 0.1 µm. The feature size of arrays synthesized by techniques disclosed herein can enable the identification of target nucleic acid positioning (e.g., the positioning of mutations, epigenetic modifications, or other features of a nucleic acid) to within about 10 µm, 9 µm, 8 µm, 7 µm, 6 µm, 5 µm, 4 µm, 3 µm, 2 µm, 1 µm, 0.9 µm, 0.8 µm, 0.7 µm, 0.6 µm, 0.5 µm, 0.4 µm, 0.3 µm, 0.2 µm, or 0.1 µm.

Reversing the Oligo Orientation Via Gel Transfer

Figure 2:
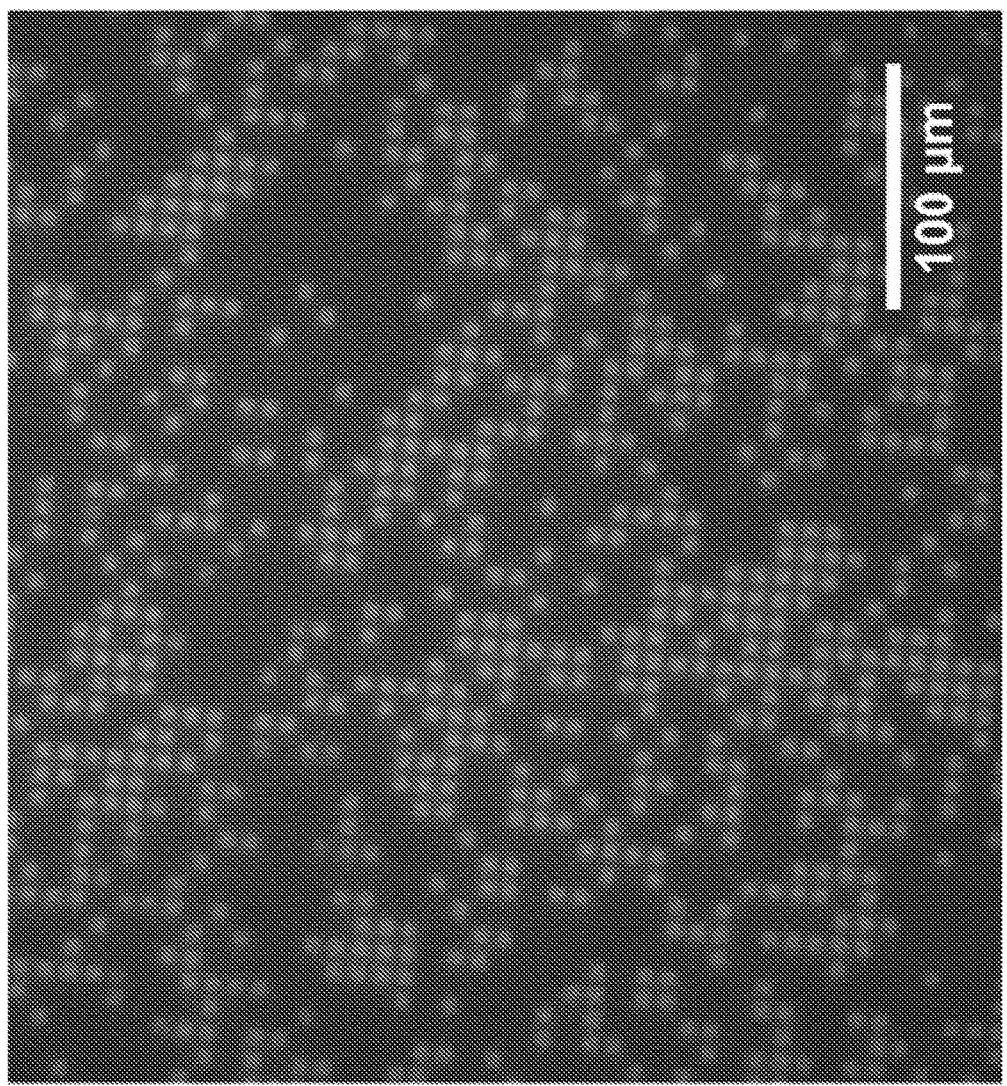
FIG. 2 illustrates an ssDNA array of 7 µm features enzymatically transferred by Bst onto a 10 µm thin acrylamide gel coated second surface and hybridized with Cy5 probe.

The standard phosphoramidite oligosynthesis using 5' DMT protecting groups can result in oligos with the 3' end attached to the surface. To serve as primers for polymerase extension on combed DNA, the oligo orientation may be reversed in some cases. A transfer method to copy the DNA array onto a second surface via face-to-face polymerase extension reaction is provided. A second surface with uniform coverage of immobilized primers complimentary to the bottom adaptor can be pressed into contact with the DNA array. The array sandwich can then be heated (e.g., to 55° C.), at which point polymerase (e.g., Bst polymerase in Thermopol PCR buffer) present at the interface can extend the primers hybridized to the bottom adaptor of the array creating a dsDNA molecular bridge between the surfaces. Upon physical separation of the arrays, the second surface can contain the complementary ssDNA barcode array with 5' end attached to the surface and 3' end available for polymerase extension. Since both the uniformly dispersed primer and the barcode oligos are tethered to their respective surfaces, the relative geographical locations of the transferred features will be maintained (in mirror image). To achieve intimate contact between the arrays, and thus uniform transfer over the full chip area, materials including PDMS and polyacrylamide have been evaluated. An exemplary result of the transfer method is shown in FIG. 2.

The methods herein can also be used to generate oligo arrays with a desired orientation. In some cases, the methods for generating oligo arrays as provided herein on surfaces prepared for generating oligo arrays as provided herein are used to generate oligo arrays that are used as templates (i.e., template arrays) for the generation of one or more oligo arrays comprising oligos coupled thereto that are complementary to oligos on the template array. The oligo arrays comprising oligos coupled thereto that are complementary to a template array can be referred to as a recipient array (or alternatively, transfer array). The transfer or recipient oligo arrays can comprise oligos with a desired orientation. The transfer or recipient arrays can be generated from the template array using an array transfer process. In some cases, template oligo arrays with a desired feature ("spot") density (e.g., feature or spot size of about 1 µm) are subjected to an array transfer process as provided herein in order to generate transfer or recipient oligo arrays with a desired orientation. The desired orientation can be a transfer or recipient oligo array that comprises oligos with the 5' end of each oligo of the array attached to the array substrate. A template oligo array for generating the transfer or recipient oligo array with oligos in a desired orientation (i.e., 5' end of each oligo of the array attached to the array substrate) can have the 3' end of each oligo of the template array attached to the substrate. The array transfer process can be a face-to-face transfer process. In some cases, the face-to-face transfer process occurs by enzymatic transfer or enzymatic transfer by synthesis (ETS). In some cases, the face-to-face transfer process occurs by a non-enzymatic transfer process. The non-enzymatic transfer process can be oligonucleotide immobilization transfer (OIT).

The face-to-face gel transfer process (e.g., ETS or OIT) can significantly reduce the unit cost of fabrication while simultaneously flipping the oligo orientation (5' immobilized) which can have assay advantages such as allowing for the enzymatic extension of the 3' ends of the array bound oligos. Moreover, ETS or OIT can result in the transfer of a greater number or higher percentage of oligos of a desired or defined length (i.e., full-length oligo) from the template array to the recipient array. Subsequent amplification (e.g., amplification feature regeneration or AFR as provided herein) of the transferred full length product oligos on the recipient oligo arrays can allow the recipient oligo arrays to contain oligos comprising greater than 50 nucleotide bases without suffering from low yield or partial length products.

In some cases, a template and/or recipient array comprises polymers. The polymers can be aptamers or oligos. In some cases, a template or recipient array comprises oligos. A template or recipient array can have coupled to it at least 10, 20, 50, 100, 200, 500, 1,000, 2,000, 5,000, 10,000, 20,000, 50,000 or 100,000, 200,000, 500,000, 1,000,000, 2,000,000, 5,000,000, 10,000,000, 20,000,000, 100,000,000, 200,000,000, 500,000,000, or 1 billion template polymers (e.g., oligos). A template array can have template polymers arranged on it at a density of at least 10, 20, 50, 100, 200, 500, 1,000, 2,000, 5,000, 10,000, 20,000, 50,000 or 100,000 polymers (e.g., oligos) per square millimeter. The polymers (e.g., oligos) on a template or recipient array can be organized into spots, regions, or pixels. Polymers (e.g., oligos) in each spot or region can be identical to each other or related to each other (e.g., all or substantially all include a consensus or common sequence). Polymers (e.g., oligos) in each spot or region can be greater than 55, 60, 65, 70, 75, 80, 85, 90, 95, 99, or 99.9% identical to each other. The template or recipient array can comprise at least 1, 2, 3, 4, 5, 6, 7, 8, 9, 10, 100, 1000, 10,000, 100,000, 1,000,000, or 10,000,000 spots or regions. Each spot or region can have a size of at most about 1 cm, 1 mm, 500 µm, 200 µm, 100 µm, 10 µm, 9 µm, 8 µm, 7 µm, 6 µm, 5 µm, 4 µm, 3 µm, 2 µm, 1 µm, 800 nm, 500 nm, 300 nm, 100 nm, 50 nm, or 10 nm.

A recipient or transfer array generated as provided herein can comprise oligos that are fully complementary, fully identical, partially complementary, or partially identical in their sequence and/or number to oligos on the template array from which the recipient array was transferred. Partially complementary can refer to recipient arrays that have at least 40%, 45%, 50%, 55%, 60%, 65%, 70%, 75%, 80%, 85%, 90%, 95%, 96%, 97%, 98%, 99%, or 99.9% sequence complementarity. Partially identical can refer to recipient arrays that have at least 40%, 45%, 50%, 55%, 60%, 65%, 70%, 75%, 80%, 85%, 90%, 95%, 96%, 97%, 98%, 99%, or 99.9% sequence identity. A recipient array can have the same number of oligonucleotides as a template array and/or at least 40%, 45%, 50%, 55%, 60%, 65%, 70%, 75%, 80%, 85%, 90%, 95%, 96%, 97%, 98%, 99%, or 99.9% of the number of oligos as the template array from which the recipient array was transferred.

Array fabrication methods as provided herein can result in arrays having polymers (e.g. oligos) of the designed, desired, or intended length, which can be called full-length products. For example, a fabrication method intended to generate oligos with 10 bases can generate full-length oligos with 10 bases coupled to an array. Array fabrication processes can result in polymers (e.g. oligos) of less than the designed, desired, or intended length, which can be called partial-length products. The presence of partial-length oligos can be within a given feature (spot) or between features (spots). For example, a fabrication method intended to generate oligos with 10 bases can generate partial-length oligos with only 8 bases coupled to an array. That is, a synthesized oligo array can comprise many nucleic acids which are homologous or nearly homologous along their length, but which may vary in length from each other. Of these homologous or nearly homologous nucleic acids, those with the longest length can be considered full-length products. Nucleic acids with length shorter than the longest length can be considered partial-length products. Array fabrication methods provided herein can result in some full-length products (e.g., oligos) and some partial-length products (e.g., oligos) coupled to an array in a given feature (spot). Partial-length products coupled to a particular array or within a given feature can vary in length. Complementary nucleic acids generated from full-length products can also be considered full-length products. Complementary nucleic acids generated from partial-length products can also be considered partial-length products.

A transfer method as provided herein (e.g., ETS or OIT) can be used to increase or enrich the amount or percentage of full-length products (e.g., oligo) coupled to a recipient array surface. Array transfer (e.g., ETS or OIT) can result in a transfer or recipient array comprising at least, at most, more than, less than, or about 30%, 40%, 50%, 55%, 60%, 65%, 70%, 75%, 80%, 85%, 90%, 95%, 96%, 97%, 98%, 99%, or 99.9% transferred oligonucleotides that are 100% of the length of the respective oligonucleotide on a template array used to generate the transfer or recipient array. A transferred oligonucleotide that is 100% of the length (i.e., the same or identical length) of a template oligonucleotide can be referred to as full-length product (e.g., full-length product oligo). A template array fabricated by methods known in that art (e.g. spotting or in situ synthesis) can comprise about 20% oligonucleotides that are a desired length (i.e., full-length oligonucleotides) and about 80% oligonucleotides that are not a desired length (i.e., partial-length oligonucleotides). Transfer of the array generated by methods known in the art comprising about 20% full-length oligonucleotides and about 80% partial-length oligonucleotides using array transfer methods as provided herein can result in the generation of transfer or recipient arrays comprising at most about 20% full-length product oligos. In some cases, an array fabricated according to the methods herein has a greater percentage of oligonucleotides of a desired length (i.e., full length oligos) such that transfer of an array fabricated according to the methods herein using array transfer methods provided herein results in the generation of transfer or recipient arrays with a higher percentage of full-length product oligos as compared to fabrication and transfer methods known in the art.

In some cases, a transfer method provided herein (e.g., ETS or OIT) comprises generation of nucleic acid (e.g., oligo) sequences complementary to the template sequences. The transfer can occur by enzymatic replication (e.g., ETS) or by non-enzymatic physical transfer (e.g., OIT) of array components between array surfaces. The array surfaces can be any array surface as provided herein. The substrate of the template array and of the recipient array can be the same or can be different. The transfer can comprise fabrication of complementary sequences which are already attached to a recipient array; for example, primers bound to a recipient array, and are complementary to adaptors on the template array, can be extended using the template array sequences as templates to thereby generate a full length or partial length recipient array. Transfer can comprise fabrication of complementary sequences from a template array followed by attachment of the complementary sequences to a recipient array.

A transfer method as provided herein (e.g., ETS or OIT) can generate a recipient array such that the orientation of a template nucleic acid (e.g., oligo) relative to its coupled recipient array surface is preserved (e.g., the 3' end of the template nucleic acid (e.g., oligo) is bound to the template array and the 3' end of the transferred nucleic acid (e.g., oligo) complement is bound to the recipient array). Transfer can reverse the orientation of a nucleic acid relative to its coupled array surface (e.g., the 3' end of the template nucleic acid is bound to the template array and the 5' end of the transferred nucleic acid complement is bound to the recipient array).

Array transfer (e.g., ETS or OIT) can be performed multiple times. Array transfer (e.g., ETS or OIT) can be performed multiple times using the same template array. A template array of template polymers bound to a template substrate can be used for the production of at least 1, 2, 3, 4, 5, 6, 7, 8, 9, 10, 20, 30, 40, 50, 60, 70, 80, 90, 100, 500, 1,000, 5,000, 10,000, 50,000, or 100,000 recipient arrays. Array transfer can be performed multiple times in a series of transfers, using the transfer array from one array transfer as the template array for a subsequent transfer. For example, a first transfer can be performed from a template array with oligonucleotides bound to the array at their 3' ends to a first transfer array with complementary oligonucleotides bound to the array at their 5' ends, and a second transfer can be performed from the first transfer array (now serving as a template array) to a second transfer array with a higher percentage of full-length products and sequences matching the original template array than in recipient arrays generated using transfer techniques commonly used in the art while preserving the 5'-surface bound orientation. In some cases, the full-length product oligos on a recipient array generated using the array transfer methods provided herein (e.g., ETS or OIT) are further enriched through amplification of the full-length product oligos on the recipient array. Amplification can be conducted using the methods provided herein. The array transfer method can be a face-to-face enzymatic transfer method (e.g., ETS) or non-enzymatic (e.g., OIT) as provided herein.

In some cases, array transfer by ETS or OIT can be aided by the use of adaptor sequences on the template polymers (e.g., oligos). Polymers (e.g., oligos) can comprise a desired final sequence with the addition of one or more adaptor sequences. For example, a template oligonucleotide can comprise, in order, a 3' end with a first adaptor sequence, a 5' end with a second adaptor sequence, and a desired final sequence in the middle. The first and second adaptor sequences can be the same or can be different. In some cases, oligonucleotides in the same array spot comprise identical first and second adaptor sequences and final sequences, and oligonucleotides in different array spots comprise identical first and second adaptor sequences but different final sequences. Primers on a transfer/recipient array can be complementary to adaptor sequences, allowing hybridization between the primers and the template polymers (e.g., oligos). Such hybridization can aid in the transfer from one array to another.

Some or all adaptor sequences can be removed from transfer/recipient array polymers (e.g. transferred oligonucleotides) after transfer, for example by enzymatic cleavage, digestion, or restriction. Some or all adaptor sequences can be removed from transfer/recipient array polymers (e.g. transferred oligonucleotides) after transfer, for example by enzymatic cleavage, digestion, or restriction. For example, oligonucleotide array components can have adaptors removed via probe end clipping (PEC) by double-strand DNAse. Oligonucleotides complementary to the adaptor sequence can be added and hybridized to the array components. DNAse specific to double-stranded DNA can then be used to digest the oligonucleotides (see FIG. 10). Alternatively, one or more cleavable base, such as a dU, can be incorporated into the primer of the strand to be removed. The primer can then be nicked at the position next to the 3'-most base of the probe, and the nick site can be cut by an appropriate enzyme, such as Mung bean S1 or P1 nuclease. Many restriction enzymes and their associated restriction sites can also be used, including but not limited to EcoRI, EcoRII, BamHI, HindIII, TaqI, NotI, HinFI, Sau3AI, PvuII, SmaI, HaeIII, HgaI, AluI, EcoRV, EcoP 15I, KpnI, PstI, SacI, SalI, ScaI, SpeI, SphI, StuI, and XbaI. In some cases, the transfer process described above is repeated from the second surface (recipient surface) to a new, third surface containing primers (e.g., oligo) complementary to the top adaptor. Because only the full length oligos can have a complete top adaptor, only these can be copied onto the third array surface (i.e., new or third recipient or transfer array). The process can purify or enrich the full length oligos from the partial products, thus creating a high feature density, high quality full length oligo array. Purification or enrichment can mean the generation of a recipient array such that said recipient array has a greater percentage or number of oligos of a desired length (i.e. full-length) than the array used as a template for the generation of said recipient array. The full-length oligos can be oligos that contain all the desired features (e.g., adaptor(s), barcode(s), target nucleic acid or complement thereof, and/or universal sequence(s), etc.).

In some cases, array transfer can be aided by the flexibility or deformability of the array (e.g., template array) or of a surface coating on the array (e.g., template array). For example, an array (e.g., template array) comprising a polyacrylamide gel coating with coupled oligonucleotides can be used in array transfer (e.g., ETS, OIT). The deformability of the gel coating can allow for array components (oligos, reagents (e.g., enzymes)) to contact each other despite surface roughness. Surface roughness can be variability in the topography of the surface.

Array components can be amplified or regenerated by enzymatic reactions termed as amplification feature regeneration (AFR). AFR can be performed on template arrays and/or recipient arrays. AFR can be used to regenerate full-length oligos on an array (e.g., template and/or recipient) in order to ensure that each oligo in a feature (spot) on an array (e.g., template and/or recipient array) comprises desired components (e.g., adaptor(s), barcode(s), target nucleic acid or complement thereof, and/or universal sequence(s), etc.). AFR can be conducted on oligos comprising adaptor and/or primer binding sites (PBS) such that the oligos each comprise a first adaptor (or first PBS), probe sequence, and second adaptor (or second PBS). Preferably, the oligos in each feature on an array (e.g., template and/or recipient array) comprise two or more primer binding sites (or adaptor sequence). AFR can be performed used nucleic amplification techniques known in the art. The amplification techniques can include, but are not limited to, isothermal bridge amplification or PCR. For example, bridge amplification can be conducted on array (e.g., template and/or recipient array) component oligonucleotides via hybridization between adaptor sequences on the array (e.g., template and/or recipient array) components and surface-bound oligonucleotide primers, followed by enzymatic extension or amplification. Amplification can be used to recover lost array (e.g., template and/or recipient array) component density or to increase density of array (e.g., template and/or recipient array) components beyond their original density.

Immobilized oligos, nucleotides, or primers on an array as provided herein (e.g., template and/or recipient array) can be equal in length to each other or can have varying lengths. Immobilized oligos, nucleotides, or primers can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 bases. In some cases, immobilized oligos, nucleotides, or primers are 71 bases long (71-mer).

The recipient surface of the transfer array can be brought into close proximity or contact with the template surface of the template array. In some cases, contact between the template array and the transfer array can be aided by the presence of a deformable coating, such as a polymer gel (e.g., polyacrylamide). The deformability of the coating can allow coupled polymers (e.g. oligonucleotides or primers) to come into close enough contact for hybridization to occur. The deformability of the coating can help overcome gaps due to surface roughness (e.g., surface topography variability) or other features that would otherwise prevent close enough contact for hybridization. An additional benefit of the deformable coating is that it can be pre-loaded with enzymatic reaction reagents, and thus serve as a reservoir for the interfacial reaction of enzymatic transfer by synthesis (ETS). One or both of the arrays can comprise a substrate with a gel coating with polymer molecules coupled to it. For example, the transfer array can comprise a substrate coupled to a polyacrylamide gel with oligonucleotide primers coupled to the gel. Surfaces and coatings are further discussed elsewhere in this disclosure.

Enzymatic Transfer by Synthesis (ETS)

ETS can comprise a face-to-face polymerase extension reaction to copy one or more template oligos (e.g., DNA oligo) from a template oligo array onto a second surface (e.g., recipient array). A second surface (e.g., recipient array) with uniform coverage of immobilized primers complimentary to sequence on an oligo in the template oligo array (e.g., the bottom adaptor sequence in oligo arrays comprising adaptor sequence) can be pressed into contact with the template oligo (e.g., DNA oligo) array. A recipient array surface can comprise surface immobilized oligomers (oligos), nucleotides, or primers that are complementary, at least in part, to template nucleic acids or oligos on the template oligo array. In some cases, a transfer or recipient array comprises oligos that selectively hybridize or bind to aptamers on a template array. Immobilized oligos, nucleotides, or primers on a transfer or recipient array can be complementary to adaptor regions on template polymers (e.g. oligos).

The template nucleic acids (oligos) can hybridize with the immobilized primers or probes on the recipient surface, also called recipient primers or probes or transfer primers or probes. The hybridized complex (e.g., duplex) can be extended enzymatically such as, e.g., by DNA polymerase including but not limited to PolI, PolII, PolIII, Klenow, T4 DNA Pol, modified T7 DNA Pol, mutated modified T7 DNA Pol, TdT, Bst, Taq, Tth, Pfu, Pow, Vent, Pab, and pyrophage.

The transfer process can preserve the orientation of the oligonucleotides, i.e. if the 5' end is bound to the template surface, the 5' end of the synthesized oligonucleotide will be bound to the recipient surface, or vice versa. Transfer primers bound at their 5' ends can bind to the template nucleic acids at their 3' ends, followed by enzymatic extension to produce nucleic acids complementary to the template oligos and bound to the recipient array surface at their 5' ends.

In some cases, only full-length template nucleic acid products are used to generate complements on the recipient array. In some cases, at least 30%, 40%, 50%, 60%, 70%, 80%, 90%, 95%, 96%, 97%, 98%, 99%, 99.9% or 100% of template nucleic acid oligos on the template array are full-length products (oligos). In some cases, at least 30%, 40%, 50%, 60%, 70%, 80%, 90%, 95%, 96%, 97%, 98%, 99%, 99.9% or 100% of transfer or recipient nucleic acid products (oligos) generated on the recipient array are full-length products. The generation of partial-length products on the recipient array during ETS can be due to incomplete extension of full-length template oligos during polymerase-driven synthesis. The generation of full-length products on the recipient arrays can be accomplished using AFR as provided herein.

In some cases, the recipient array includes on it primers that hybridize a portion of the template polymers (e.g., oligos) such that extension reactions occur until all of the template polymers (e.g., oligos) are used as templates for synthesis of a complementary recipient oligos on a complementary array (or recipient array). In some instances, synthesis of the recipient array occurs such that on average at least 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, or 50% of the template polymers (e.g., oligos) are used to generate complementary sequences on the recipient array. Stated differently, a recipient array, post-transfer, can comprise recipient nucleotides (e.g., oligos) synthesized using at least 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, or 50% of the template oligonucleotides as templates.

The array transfer process (e.g., ETS) can invert the orientation of the template nucleic acids. That is, if the 5' end is bound to the template surface, the 3' end of the synthesized oligonucleotide will be bound to the recipient surface, or vice versa.

Template nucleic acids (e.g., oligos) bound to the template array surface (template surface) at their 3' ends can hybridize to transfer primers on the recipient array bound to the recipient array surface at their 5' ends. Enzymatic extension of the transfer primers produces nucleic acids (e.g., oligos) complementary to the template nucleic acids (e.g., oligos) and bound to the recipient array surface at their 5' ends. In some cases, partial-length oligos in a feature (spot) of the template array) are utilized to generate complementary partial length oligos on a recipient array. In some cases, full-length oligos in a feature (spot) of the template array are utilized to generate complementary full-length oligos on a recipient array.

The template and recipient surfaces can be biocompatible, such as polyacrylamide gels, modified polyacrylamide gels, PDMS, silica, silicon, COC, metals such as gold, chrome, or chromium, or any other biocompatible surface. If the surface comprises a polymer gel layer, the thickness can affect its deformability or flexibility. The deformability or flexibility of a gel layer can make it useful in maintaining contact between surfaces despite surface roughness. Details of the surfaces are further discussed herein.

Reagents and other compounds including enzymes, buffers, and nucleotides can be placed on the surface or embedded in a compatible gel layer. The enzymes can be polymerases, nucleases, phosphatases, kinases, helicases, ligases, recombinases, transcriptases, or reverse transcriptases. In some cases, the enzymes on the surface or embedded in a compatible gel layer comprise a polymerase. Polymerases can include, but are not limited to, PolI, PolII, PolIII, Klenow, T4 DNA Pol, modified T7 DNA Pol, mutated modified T7 DNA Pol, TdT, Bst, Taq, Tth, Pfu, Pow, Vent, Pab, Phusion, pyrophage and others. Details of the surfaces are further discussed herein. In some cases, the enzymes on the surface or embedded in a compatible gel layer comprise a ligase. Ligases can include, but are not limited to, E. coli ligase, T4 ligase, mammalian ligases (e.g., DNA ligase I, DNA ligase II, DNA ligase III, DNA ligase IV), thermostable ligases, and fast ligases.

The surface of the recipient array can be a gel formed on top of the template array. The reaction mixture can be placed on the surface of the recipient array or embedded in a recipient surface. In some cases, the reaction mixture is placed on the surface of the recipient array. In some cases, the reaction mixture is embedded in the recipient surface. The recipient surface can be a compatible gel layer. The reaction mixture can comprise any reagent necessary to conduct enzymatic transfer by synthesis (ETS).

Enzymatic transfer of a template array by ETS can be conducted as follows: 1.) enzyme mix is prepared (e.g., 37 μL H$_2$O, 5 μL 10× Thermopol buffer, 5 μL of 10 mg/mL BSA, 1 μL of 10 mM dNTPs, and 2 μL of 8 U/μL Bst enzyme); 2.) enzyme mix is applied to a recipient array (e.g., an acrylamide gel coated glass slide with coupled oligonucleotide primers prepared as described elsewhere in this disclosure); 3.) a template array is placed face-to-face with the and allowed to react (e.g., clamped together in a humidity chamber for 2 hours at 55° C.); 4.) the template and recipient arrays are separated (e.g., loosened by application of 4×SSC buffer and pulled apart with the aid of a razor blade); 5.) the template array is rinsed (e.g., in DI water) and dried (e.g., with N$_2$); and 6.) the recipient array is rinsed (e.g., with 4×SSC buffer and 2×SSC buffer). In some cases, the oligos on the template array comprise adaptors, such that a bottom adaptor is located proximal to the template array surface, while a top adaptor is located distal from the template array surface. While the sandwich is heated to 55° C., Bst polymerase in Thermopol PCR buffer can extend the primers from the recipient array hybridized to the bottom adaptor of the template array, which can create a dsDNA molecular bridge between the template and recipient array surfaces. Upon physical separation, the second surface (i.e., recipient array) can contain the complementary ssDNA barcode array with the 5' end of the oligos attached to the surface and the 3' end available for polymerase extension. Since both the uniformly dispersed primer on the template array and the barcode oligos on the recipient array can be tethered to their respective surfaces, the relative locations of the transferred features can be maintained (in mirror image). To achieve intimate contact and thus uniform transfer over the full chip area, a broad range of surface materials (PDMS, Polyacrylamide), thicknesses, and process conditions can be used. The efficiency of face-to-face transfers can result in reduced density of oligos within each copied array feature. One of skill in the art can appreciate that the transfer conditions can be optimized by, for example, varying the gel transfer conditions, e.g. choice of enzyme, process temperature and time, length of primers, or surface material properties. Alternatively, post-transfer surface amplification via solid-phase PCR (e.g. bridge-PCR) can be used increase the barcode density to the desired level as described herein.

Oligonucleotide Immobilization Transfer (OIT)

In some instances, the generation of a recipient array is performed by non-enzymatic transfer. One form of non-enzymatic transfer is oligonucleotide immobilization transfer (OIT). In OIT, the template nucleic acids (e.g., oligo) on a template array can be single-stranded. Primers comprising sequence complementary to a portion of the template oligos can hybridize to the template oligos and be extended by primer extension in order to generate and can be made double-stranded template oligos on the template array. The primers used for primer extension can be in solution. Many polymerases can be used for OIT, including PolI, PolII, PolIII, Klenow, T4 DNA Pol, modified T7 DNA Pol, mutated modified T7 DNA Pol, TdT, Bst, Taq, Tth, Pfu, Pow, Vent, Pab, Phusion and others. In some cases, the primers used for primer extension comprise linkers that are used to immobilize or bind strand of the double-stranded template oligo generated by primer extension on a surface of a recipient array. The recipient array surface can be a planar surface, a bead, or a gel as provided herein. In some cases, the recipient array surface is a polyacrylamide gel formed during OIT. In some cases, subsequent to extension, the linkers can be bound to a recipient array surface. The recipient array surface can be any array surface as provided herein such as a polymer gel or modified glass surface. In OIT, the template and recipient array surfaces can be then be separated. The DNA (i.e., double-stranded template oligos) can be melted prior to separation.

In some cases, the primers used in OIT are 5'-acrydite modified primers. The 5'-acrydite modified primers can be capable of incorporation into a polymer gel (e.g., polyacrylamide) during polymerization as provided herein. Extension products from the template nucleic acids (e.g., oligos) can then be generated with the acrydite primers, contacted with a substrate with a binding treatment (e.g., unpolymerized polyacrylamide coating precursor), incorporated during polymerization, and separated. The primers can be 5'-hexynyl-polyT-DNA. In some cases, primer extension products from the template nucleic acids are generated via binding and extension of complementary 5'-hexynyl-polyT-DNA primers. Following extension, the 5'hexynyl-polyT-DNA primers can be: 1) contacted with a substrate with a binding treatment (such as glass treated with silane), 2) linked to a cross-linker such as, for example, a homobifunctional linker such as 1,4-Phenylene Diisothiocyanate (PDITC), 3) linked to an N3 bonding group with a PEG linker, 4) bonded to the substrate at the N3 group, and 5) separated during a second stage of OIT. The surfaces can be any of the surfaces as discussed herein. Other cross-linkers that can be used in place of PDITC can include dimethyl suberimidate (DMS), disuccimidyl carbonate (DSC) and/or disuccimidyl oxylate (DSO). This process can preserve the orientation of the oligonucleotides, i.e. if the 5' end is bound to the template array surface, the 5' end of the synthesized oligonucleotide will be bound to the recipient array surface, or vice versa. While enzymatic extension can be used prior to the transfer, the transfer itself can be conducted without enzymatic reactions.

In some cases, an oligo array with 5' to 3' orientation can be generated without enzymatic transfer. For example, the unbound end of the synthesized nucleic acid sequences on a template oligo array can comprise a linker sequence complementary to a sequence at or near the array-bound end of the oligo, allowing the oligo to circularize. The oligo can further comprise a restriction sequence at the same end. Digestion of the restriction sequence on circularized oligos serve to flip the full-length oligos containing the linker sequence and cut loose any partial-length oligo products on the array which lack the linker sequence. Many restriction enzymes and their associated restriction sites can be used, including but not limited to EcoRI, EcoRII, BamHI, HindIII, TaqI, NotI, HinFI, Sau3AI, PvuII, SmaI, HaeIII, HgaI, AluI, EcoRV, EcoP15I, KpnI, PstI, SacI, SalI, ScaI, SpeI, SphI, StuI, and XbaI.

Selecting for Full-Length Probes

Due to inefficiencies of deprotection and coupling, existing array synthesis technologies can suffer from partial length product. This can be especially problematic for longer oligos, where a stepwise efficiency of 98% yields only 36% full length 50-mers oligos, with the rest being truncated. The transfer process described above from surface two to a new third surface containing primers complementary to the top adaptor can help purify full length probes. Because only the full length oligos will have a complete top adaptor, only these will be copied onto the third surface. The process can purify the full length oligos from the partial products, thus creating a high feature density, high quality, full length DNA array.

The epigenetic modifications (e.g., 5-methylcytosine) can be labeled using an antibody, and specifically capture the genomic regions that contain an epigenetic modification. The genomic regions that contain epigenetic modifications can be captured for library construction, while maintaining the relative position of these library molecules. The relative positions can allow phasing of epigenetic modifications across long genomic distances.

Isolating Long DNA Molecules

Methods for extracting Mb long DNA are known (see, e.g., Zhang, M. et al. Preparation of megabase-sized DNA from a variety of organisms using the nuclei method for advanced genomics research, Nature protocols 7, 467-478, (2012), incorporated here by reference) and routinely performed in many labs. For example, the BioRad Mammalian Genomic DNA Plug Kit can be used. Briefly, the plug can be washed and the agarose can be melted and digested (e.g., with a beta-agarase). The DNA solution can then be processed as described below.

Processing DNA Prior to Combing

Figure 3A:
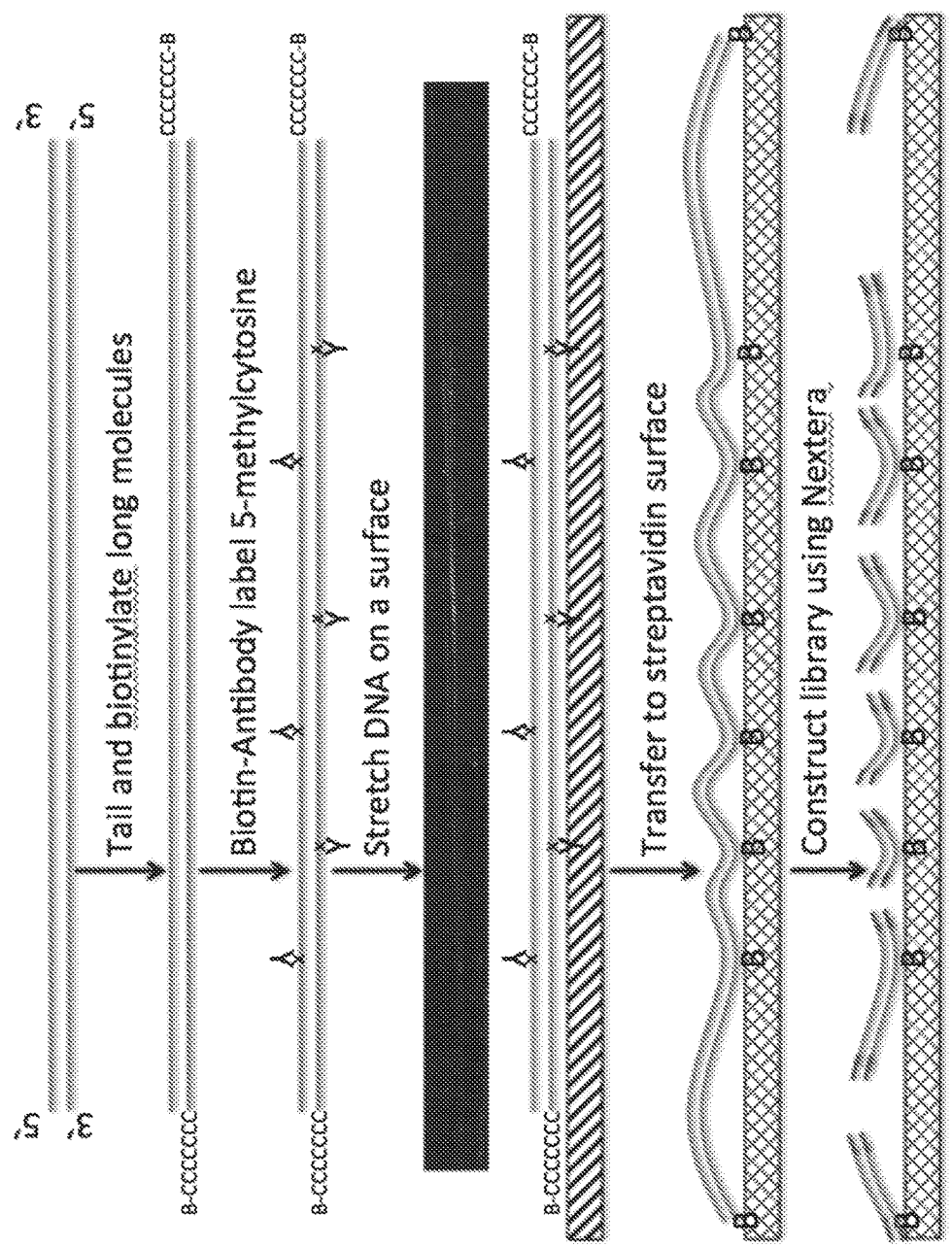
FIG. 3A shows process steps including first isolating long DNA molecules; adding poly-C tails and biotin at the 3' end of the long molecules to specifically capture the end sequences; labelling the epigenetic modifications with an antibody either pre- or post-stretching; transferring of the molecules to a streptavidin coated surface; and creating Nextera libraries in situ.

The long DNA molecules can be processed prior to combing in order to attach primer sites and biotin to the ends of the long DNA molecules, as shown for example in FIG. 3A. The process can be designed to be performed with a minimal number of steps, to keep the DNA molecules as long as possible, and to attach primer sites at the end of the DNA, thereby enabling specific generation of library reads from the ends of the immbolized DNA molecules which can assist the analysis. The DNA can be diluted in 0.5M pH 5.5 buffer and poured into a stretching reservoir to prepare it for combing.

DNA Combing

Immobilization of intact, megabase-long DNA molecules by combing can resolve the sequence in complex repetitive regions of the genome (in some regions, for the first time). Such techniques can further reduce the sequencing costs associated with WGS. DNA combing can be performed in a variety of ways including using microfluidic channels. There are numerous methods for combing chromosomal DNA on surfaces or through microfluidic channels.

Multiple copies of individual long DNA molecules can be combed or otherwise stretched on a surface. For example, at least 2, 5, 10, 20, 50, 100, 200, 500, 1,000, 2,000, 5,000, 10,000, 20,000, 50,000, 100,000, 200,000, 500,000, or 1,000,000 individual DNA molecules can be stretched on a surface. Multiple stretched DNA molecules can be probed or otherwise analyzed for epigenetic modifications in parallel. The surface density of DNA molecules can be at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 genomes per square centimeter (genome/cm$^2$). In some cases, the density of DNA molecules on the surface is from about 25 to about 50 genomes per cm$^2$. The coverage of DNA molecules can be at least about 1×, 2×, 3×, 4×, 5×, 6×, 7×, 8×, 9×, 10×, 11×, 12×, 13×, 14×, 15×, 16×, 17×, 18×, 19×, 20×, 25×, 30×, 35×, 40×, 45×, 50×, 55×, 60×, 65×, 70×, 75×, 80×, 85×, 90×, 95×, or 100× diploid genome coverage. In some cases, the density of DNA molecules on the surface is from about 30× to about 40× diploid genome coverage. The surface can comprise DNA fragments that are at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 megabases (Mb) in length. For example, DNA fragments can be from about 1 to about 40 Mb in length.

Molecular combing method for stretching and immobilizing DNA (Gueroui, Z., Place, C., Freyssingeas, E. & Berge, B. Observation by fluorescence microscopy of transcription on single combed DNA. Proceedings of the National Academy of Sciences of the United States of America 99, 6005-6010, (2002); Bensimon, A. et al. Alignment and sensitive detection of DNA by a moving interface. Science 265, 2096-2098, (1994); incorporated herein by reference). Molecular combing is a process through which free DNA in a solution can be placed in a reservoir, and a hydrophobic-coated slide (e.g., polylysine) can be dipped into the DNA solution and retracted. The process of retracting the slide produces a receding meniscus which can pull the DNA in a linear fashion (see, e.g., FIG. 4A, FIG. 4B, FIG. 4C, & FIG. 5) (Bensimon, A. et al. Alignment and sensitive detection of DNA by a moving interface. Science 265, 2096-2098, (1994); Michalet, X. et al. Dynamic molecular combing: stretching the whole human genome for high-resolution studies. Science 277, 1518-1523, (1997), incorporated here by reference). In some cases, the DNA can be combed on a first surface (e.g., PDMS), and then transferred to a second surface (e.g., polylysine) for labeling.

In some cases, a target polynucleotide for use in the methods provided herein is stretched. The target polynucleotide can be DNA. Stretching can be performed by various methods, including but not limited to molecular combing, transfer printing, molecular threading, nanochannels, electric force, magnetic force, optical force, and hydrodynamic force. Stretching can be performed by a combination of methods. For example the use of molecular combing and nanochannels. DNA stretching can be a process through which DNA in a solution ("free DNA") can be placed in a reservoir, and a hydrophobic-coated slide can be dipped into the DNA solution and retracted. While the physics of the process may not be fully understood, the DNA ends can interact with the surface of the slide through hydrophobic interactions, and the process of retracting the slide can produce a receding meniscus which can serve to pull the DNA across a surface in a linear fashion. DNA stretching can be a highly parallel process that can produce high-density packed DNA molecules stretched on a surface or substrate. One of skill in the art can appreciate that DNA stretching can be performed on a variety of surfaces, and specific conditions for stretching on specific surfaces can be optimized using methods known in the art. The variety of surfaces or substrates can be glass, silicon, and/or polymers or polymer-coated surfaces. Stretching substrates can comprise features, such as microchannels, nanochannels, microposts, or nanoposts. The stretching substrate can be the same as the primer array or can be a separate substrate. The DNA molecules can range in size from several hundred kb to more than 1 Mb. Immobilization of intact, several kb to Mbase length target polynucleotides (e.g., DNA molecules) by stretching can provide the ability to resolve sequence in complex repetitive regions of a genome, and can further reduce the sequencing costs associated with WGS. Stretching can provide improved access for hybridization to the template nucleic acid molecule. Stretching can increase the linearity of the template nucleic acid molecule. Stretching nucleic acids can increase the resolution or distance between regions of the nucleic acid. Stretching can increase the length of DNA to 1.5 times the crystallographic length of DNA. Once a target polynucleotide (e.g., DNA) has been stretched and bound to a solid surface, it can be probed to create scaffolds for assembling the short NGS reads as described herein. The template nucleic acids can be stretched on an oligo array (e.g., template or recipient oligo arrays).

While stretching can occur in solution or on a substrate, the stretched target polynucleotide can be eventually laid upon or can be positioned in an elongated fashion upon a substrate. The array substrates can be template and/or recipient oligo arrays as described herein.

The stretching substrate can comprise a surface coating or functionalization. The surface coating or functionalization can be hydrophobic or hydrophilic. The stretching substrate can be an amine derivatized glass slides with a poly)maleic anhydride)-based comb-copolymer). The surface coating can comprise a polymer coating, such as polyacrylamide. The surface coating can comprise a gel, such as a polyacrylamide gel. The surface coating can comprise metal, such as patterned electrodes or circuitry. The surface coating or functionalization can comprise a binding agent, such as streptavidin, avidin, antibodies, antibody fragments, or aptamers. The surface coating or functionalization can comprise primers, e.g., for elongating fragments of the stretched nucleic acid. The surface coating or functionalization can comprise multiple elements, for example a polymer or gel coating and a binding agent, or a polymer gel coating and primers. The stretching substrate can comprise a primer array. Primer arrays are further discussed elsewhere in this disclosure.

In some cases, stretching of a target polynucleotide as provided herein is by transfer printing. The transfer printing method can be one such as the one described in Zhang et al., 2005, *Langmuir* 21:4180-4184, the disclosure of which is hereby incorporated by reference in its entirety. Stretched nucleic acids can be prepared and aligned on a stamp, such as a PDMS stamp, by stretching with molecular combing. Nucleic acids stretched on the stamp can be anchored or bonded to the surface, for example by amino-terminated surface modification. Contact or transfer printing can be used to transfer aligned nucleic acids from the stamp to a surface. In some cases, the meniscus speed can influence the nucleic acid density on the surface.

In some cases, stretching of a target polynucleotide as provided herein is by molecular threading. The molecular threading method can be one such as the one described in Payne et al., 2013, *PLoS ONE* 8:e69058 the disclosure of which is hereby incorporated by reference in its entirety. A droplet of nucleic acid molecules (e.g., DNA molecules) in solution can be positioned near a surface. A probe, such as a PMMA-treated glass needle, can be used to grab individual nucleic acid molecules (e.g., DNA molecules) in the solution. The probe can then be pulled from the solution, stretching the associated nucleic acid molecule (e.g., DNA molecule). The stretched nucleic acid molecule (e.g., DNA molecule) can then be deposited on a surface. In some cases, stretched nucleic acid molecules (e.g., DNA molecules) can be placed less than or equal to about 100 nm apart.

In some cases, stretching of a target polynucleotide as provided herein is performed by use of nanochannels. The stretching through the use of nanochannel can be such as described in Reisner et al., 2012, *Rep. Prog. Phys.*, 75(10): 106601 or in U.S. Pat. No. 7,670,770 the disclosures of which are each hereby incorporated by reference in their entireties. Nanochannels can be about 200, 190, 180, 170, 160, 150, 140, 130, 120, 110, 100, 90, 80, 70, 60, 50, 40, 30, 20, or 10 nm in width, height, diameter, or hydrodynamic radius. Nanochannels can be formed in materials including polymer, glass, and silicon. Nucleic acid molecules (e.g., DNA molecules) can stretch out when confined in nanochannels, due to self-avoidance interactions. Extension or stretching of nucleic acids (e.g., DNA) in nanochannels can depend on the ionic strength of the nucleic acid (e.g., DNA) solution.

In some cases, stretching of a target polynucleotide as provided herein is performed by use of nanostructures. The stretching through the use of nanostructures can be such as described in U.S. Pat. No. RE42315, the disclosure of which is hereby incorporated by reference in its entirety. Nanostructures on a substrate can comprise nanotroughs, and the substrate can have a lipid bilayer suspended on it. Nucleic acid molecules (e.g., DNA molecules) can be driven through the membrane into the troughs and stretched.

In some cases, stretching of a target polynucleotide as provided herein is performed by magnetic force (such as magnetic tweezers). The magnetic force method can be one such as the one described in Haber and Wirtz, 2000, *Rev. Sci. Instrum.* 71:4561, the disclosure of which is hereby incorporated by reference in its entirety. Nucleic acid molecules (e.g., DNA molecules) can be linked to a magnetic particle or bead, which can then be manipulated with an applied magnetic field. Applied magnetic force can be used to stretch the nucleic acid molecule (e.g., DNA molecule), for example while one end of the molecule is linked to a magnetic particle and the other end of the molecule is linked or tethered to a substrate.

In some cases, stretching of a target polynucleotide as provided herein is performed by optical force (such as optical tweezers). The optical force method can be one such as the one described in Wang et al., 1997, *Biophysical Journal*, 72(3): 1335-1346, the disclosure of which is hereby incorporated by reference in its entirety. Nucleic acid molecules (e.g., DNA molecules) can be linked to a particle or bead, which can then be manipulated with an optical trap. The optical trapping force can be used to stretch the nucleic acid molecule (e.g., DNA molecule), for example while one end of the molecule is linked to a trapped particle and the other end of the molecule is linked or tethered to a substrate.

In some cases, stretching of a target polynucleotide as provided herein is performed by electrical fields. The electrical fields method can be one such as the one described in Ferree and Blanch, 2003, *Biophysical Journal*, 85(4):2539-2546, the disclosure of which is hereby incorporated by reference in its entirety. Nucleic acid molecules (e.g., DNA molecules) can be tethered to a substrate, such as by biotin-streptavidin binding or other methods. An applied electric field can then be used to generate a force to stretch the molecules.

In some cases, stretching of a target polynucleotide as provided herein is performed by hydrodynamic force. The hydrodynamic method can be one such as the one described in Kim et al., 2007, *Nature Methods*, 4:397-399, the disclosure of which is hereby incorporated by reference in its entirety. Target polynucleotides can be tethered to a substrate, such as by biotin-streptavidin binding or other methods. Fluid flow around the target polynucleotides can provide force to stretch the molecules.

In some cases, target polynucleotides can be stretched on a stretching substrate and then contacted with a primer array (e.g., template and/or recipient oligo array). Alternatively, target polynucleotides can be stretched directly on a primer array (e.g., template and/or recipient oligo array).

Immobilizing DNA on First Surface and Labeling the Epigenetic Modifications for Capture on a Second Surface Once DNA has been stretched and bound to a solid surface, the DNA can be probed to create scaffolds for assembling the short NGS reads. This can allow for unbiased long read sequencing. Epigenetic modifications (e.g., 5-methyl cytosine) can be labeled, for example by using an antibody. The genomic regions that contain epigenetic modifications can be captured. Sequencing libraries from the immobilized and captured DNA on an oligonucleotide positional barcode array can be prepared using routine biochemistry. These libraries can be sequenced (for example, using an Illumina HiSeq). The barcodes can be sequenced and can provide a scaffold for placing the epigenetic modifications on long individual DNA molecules.

This disclosure provides methods and compositions for immobilization of nucleic acids on a substrate. Optionally, immobilization can be used to help separate extension or amplification products from the template nucleic acid ("target polynucleotide"). In some cases, a target polynucleotide is immobilized to an immobilization substrate.

Many different materials are suitable for use as the immobilization substrate. The immobilization substrate can comprise glass, silicon, polymer (e.g. polyacrylamide, PMMA), or metal. The immobilization substrate can comprise physical features, such as microchannels or nanochannels.

The immobilization substrate can comprise a surface coating or functionalization. The surface coating or functionalization can be hydrophobic or hydrophilic. The surface coating can comprise a polymer coating, such as polyacrylamide. The surface coating can comprise a gel, such as a polyacrylamide gel. The surface coating can comprise metal, such as patterned electrodes or circuitry. The surface coating or functionalization can comprise a binding agent, such as streptavidin, avidin, antibodies, antibody fragments, or aptamers. The surface coating or functionalization can comprise multiple elements, for example a polymer or gel coating and a binding agent.

Figure 4A:
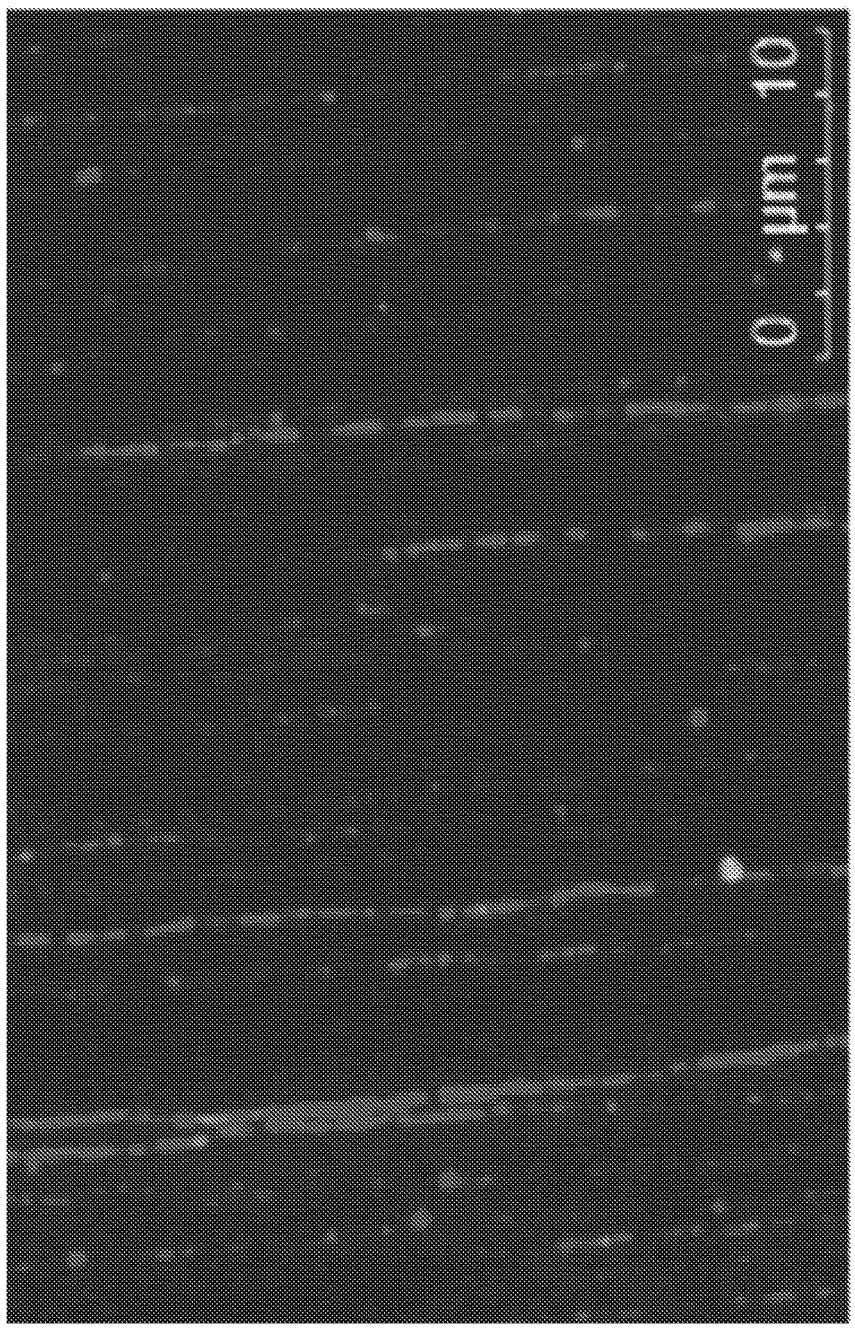
FIG. 4A illustrates denatured dsDNA using 0.5M NaOH; ssDNA was probed with anti-ssDNA antibody.
Figure 4B:
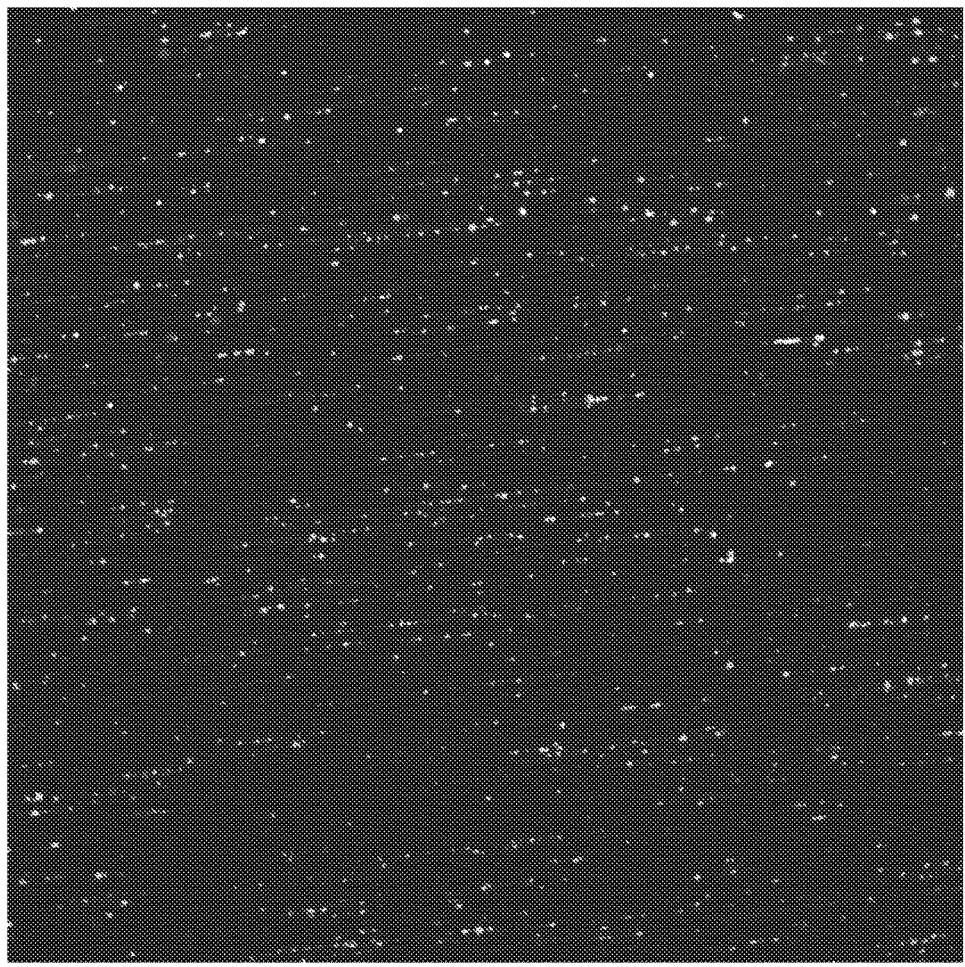
FIG. 4B illustrates polymerase extension of immobilized DNA; Vent polymerase extended primed immobilized ssDNA. The blue stain is YOYO. Green is a BIO oligo primer. Red is a DIG dGTP incorporated by vent.
Figure 4C:
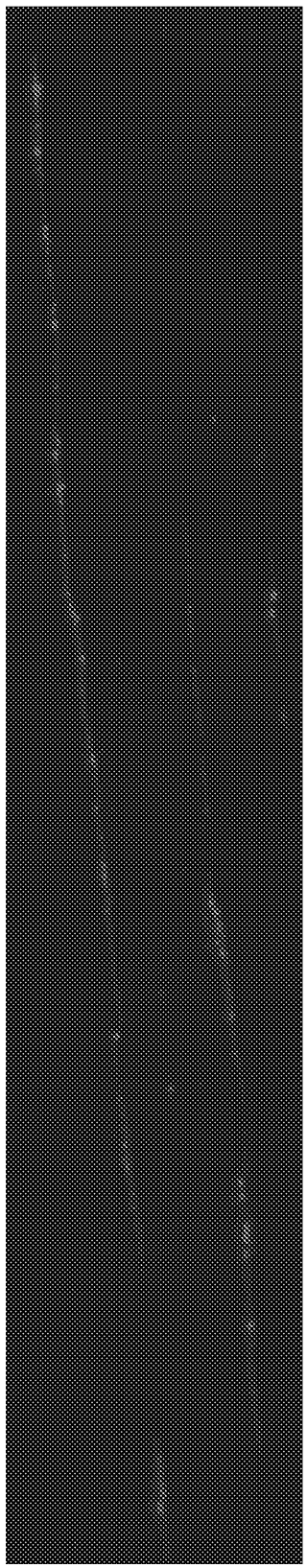
FIG. 4C illustrates DNA molecules immobilized on a surface with YOYO staining (blue). 5-methylcytosine is probed with an antibody and visualized with a Cy-5 labeled secondary antibody (red).
Figure 5:
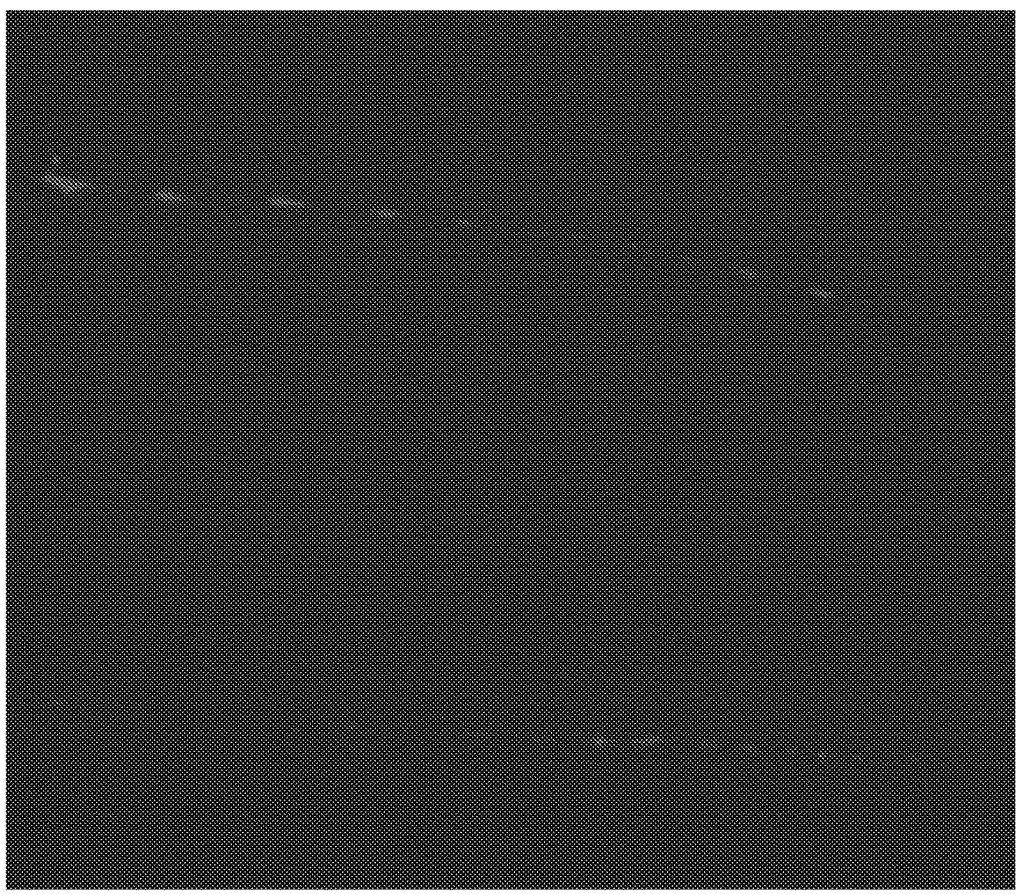
FIG. 5 illustrates incorporation of fluorescent dUTP using Bst polymerase.
Figure 6:
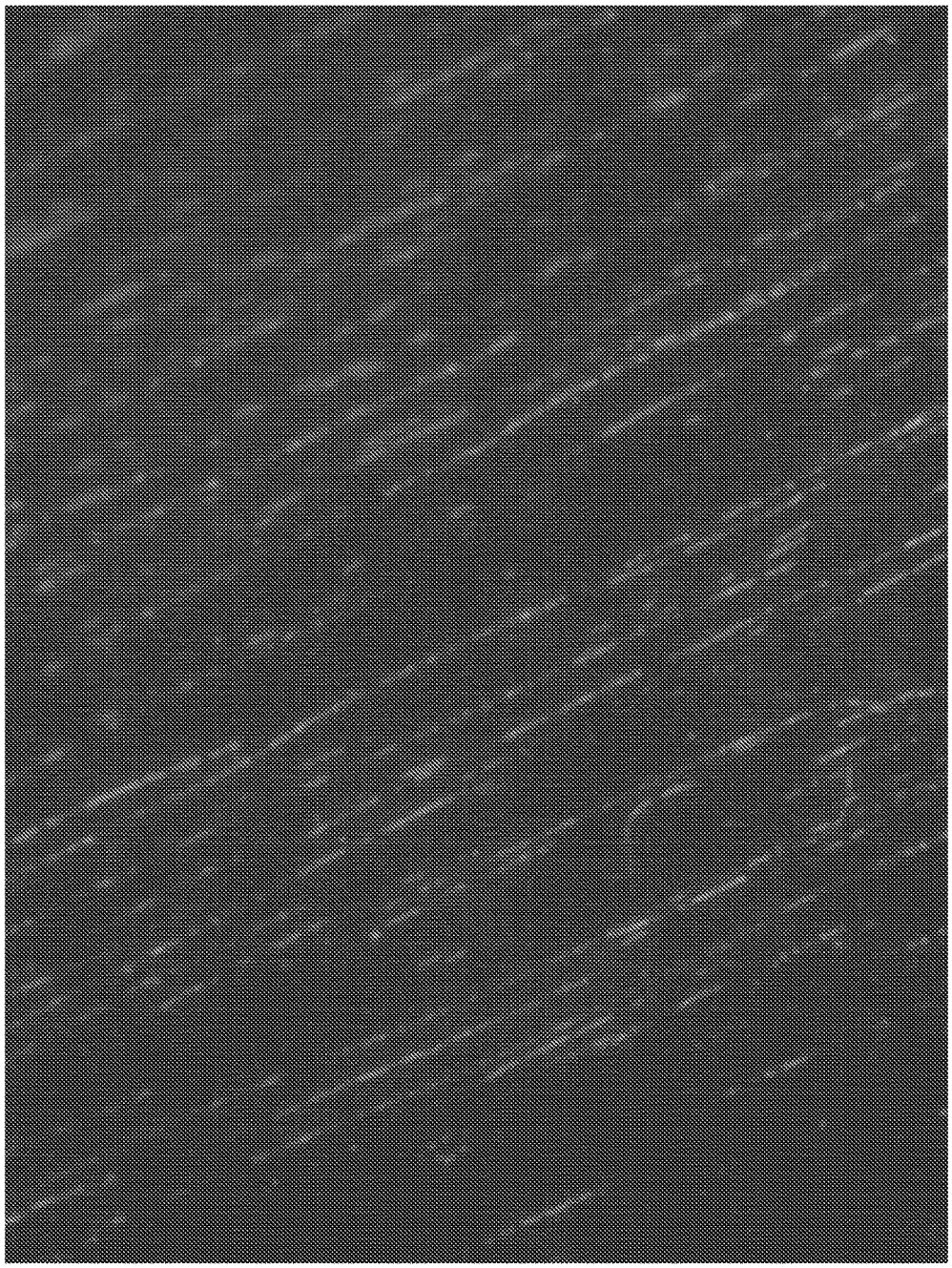
FIG. 6 shows combed DNA is labeled in green and 5-methylcytosine labeled in red.

Following DNA combing, the hydrophobic surface can be blocked (e.g., with BSA) and the epigenetic modifications can be labeled (e.g., with biotin). Epigenetic modifications can be labeled with a range of labels and affinity agents, such as by using an antibody specific for the epigenetic modification of interest (e.g., 5-methylcytosine). Affinity agents, such as antibodies, can be labeled (e.g., with biotin), to allow labeling of epigenetic modifications. FIG. 4A shows an exemplary result of using an antibody to identify combed regions of ssDNA. Any epigenetic modification for which an antibody or other label can be developed may be targeted and labeled with such techniques.

At least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 different epigenetic modifications can be labeled on a nucleic acid (e.g., combed DNA). Multiple instances of the same modification can be labeled, as well as different modifications.

Transfer DNA to Second Surface and Library Construction.

The immobilized DNA molecules can be transferred to a streptavidin coated surface (e.g., streptavidin embedded within a hydrogel). The streptavidin surface can capture the biotin-labeled epigenetic modifications as well as the biotinylated ends of the immobilized DNA molecules (see, e.g., FIG. 3A). A sequencing library from the molecules bound to the streptavidin surface can be created, for example, using a Nextera reaction (commercially available from Illumina, San Diego). Sequencing libraries can also be created by other techniques, such as ligation and PCR (see, e.g., FIG. 7A and FIG. 7B). This can generate library molecules that contain epigenetic modifications on the surface and these library molecules can be spatially constrained so as to scaffold the epigenetic modifications along long single DNA molecules. Library molecules can contain spatial barcode information as well as genetic or epigenetic information.

Figure 7A:
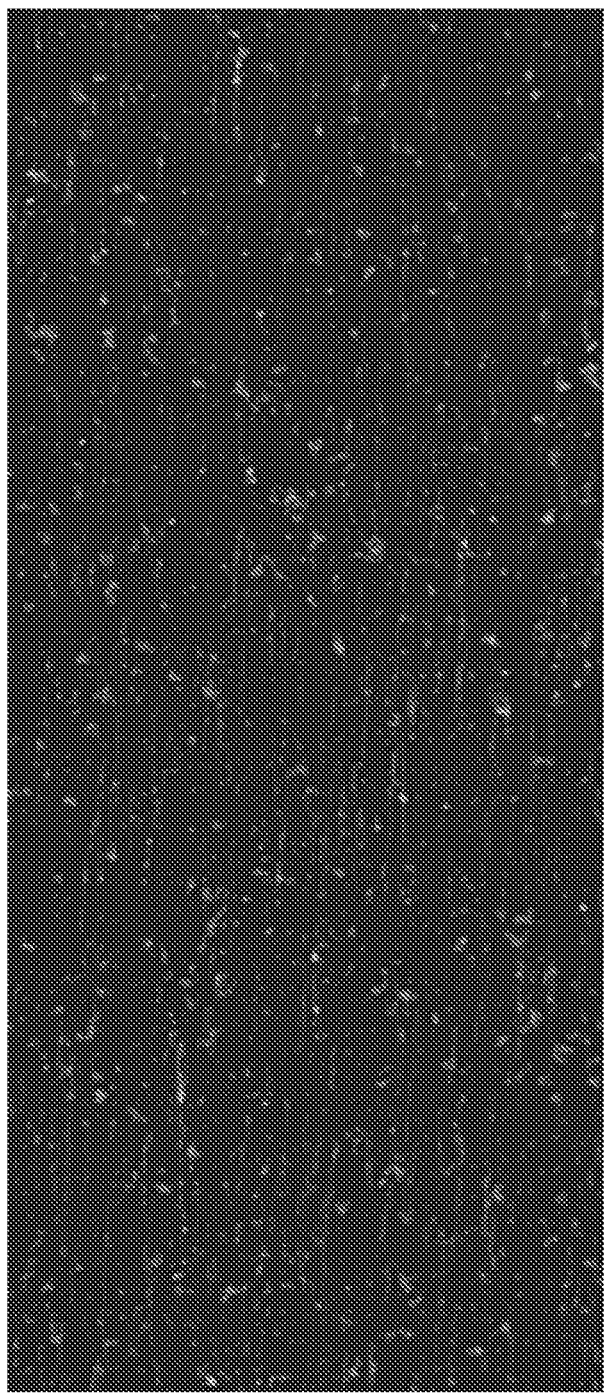
FIG. 7A shows combed DNA molecules (50 pg/µL) on a surface.
Figure 7B:
FIG. 7B shows a gel demonstrating library molecule size for a library generated from combed DNA molecules.

FIG. 7A shows combed DNA molecules (about 50 pg/μL) that were converted into a library on a DNA chip surface. The library was created by cutting the stretched DNA with a 6-base cutter and ligating to array oligonucleotides, resulting in the large library molecule size shown in the gel pictured in FIG. 7B. The library was extracted from the array by PCR amplification and collection of the liquid following amplification. Libraries generated by a similar technique (using a 4-base cutter) were sequenced on a MiSeq and ~20% of the reads mapped to the Human Genome, while the other 80% of the reads were easily identified as oligonucleotides from the DNA chip.

Sequencing libraries can be generated from the immobilized and captured DNA on an oligonucleotide array. Libraries can then be sequenced, for example on an Illumina HiSeq. The barcodes can also be sequenced, which can provide a scaffold for placing the epigenetic modifications on each long individual DNA fragment that is immobilized on a surface. The absence of epigenetic modifications can also be recognized by the absence of library molecules between the ends of a DNA fragment.

Extend Immobilized dsDNA.

Figure 3B:
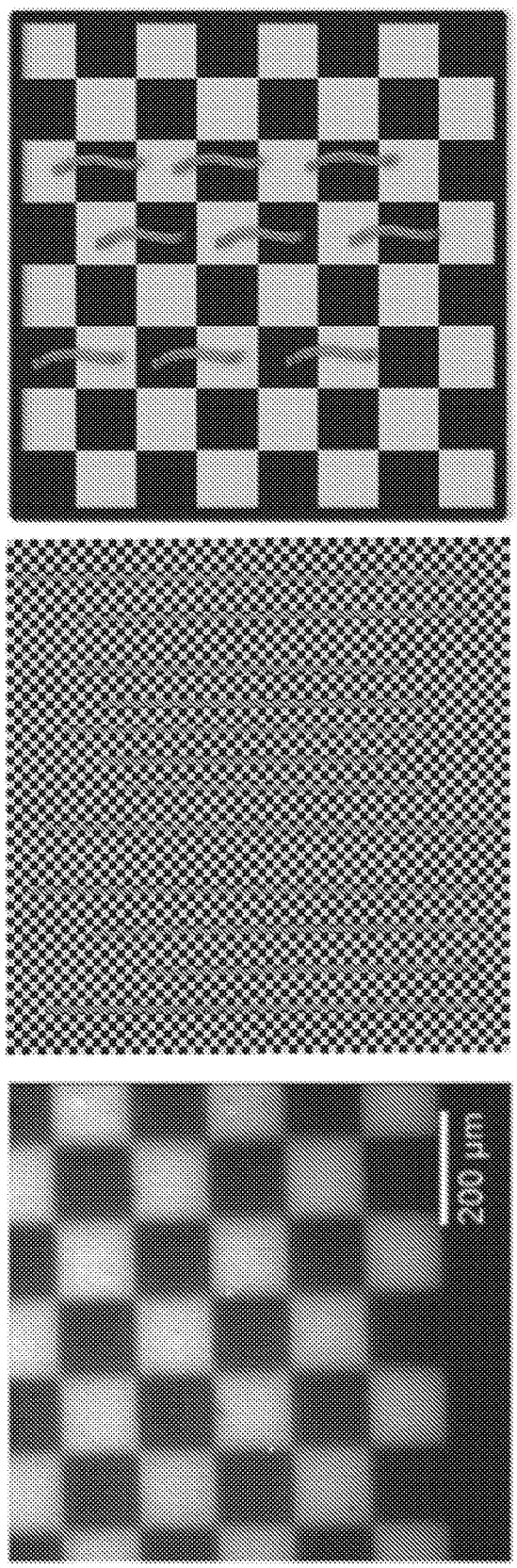
FIG. 3B shows transfer of the library molecules to a chip for barcoding.

The dsDNA libraries produced can have primer sites allowing generation of complementary strands on the array surface (see, e.g., FIG. 3B). The ssDNA on the array surface can prime the sites on the library molecules and can be extended while immobilized (see, e.g., FIG. 3B). Primers can be extended while annealed to DNA and transfer DNA to the chip surface using a polymerase (see, e.g., FIG. 4A, FIG. 4B, FIG. 4C & FIG. 5). The process can be conducted with no (or minimal) bias in the regions that are extended.

Once target polynucleotides are isolated and processed as provided herein, positional barcoded extension products can be generated from the target polynucleotides. In some cases, target polynucleotides processed as provided herein are stretched on a stretching substrate and contacted with primers on a primer array (e.g., template and/or recipient oligo array) prior to being subjected to primer extension reactions.

A primer substrate comprising a gel surface coating can be brought into contact with a stretching substrate comprising stretched target polynucleotides. Alternatively, target polynucleotides can be stretched, immobilized on an immobilization substrate, and contacted with primers on a primer array (e.g., template and/or recipient oligo array). Alternatively, target polynucleotides can be stretched directly on a primer array (e.g., template and/or recipient oligo array) substrate. Primers on the primer array (e.g., template and/or recipient oligo array) can hybridize to primer binding sites introduced into target polynucleotides using the methods provided herein.

Extension reactions can be conducted to extend primers hybridized to a target polynucleotide using segments of the target polynucleotide as template. The target polynucleotide can be a stretched target polynucleotide. The primers hybridized to the target polynucleotide (e.g. stretched polynucleotide) can be non-substrate bound (i.e., free in solution) or substrate bound. In some cases, extension reactions are performed with primers bound to a primer array (e.g., template and/or recipient oligo array) to generate positionally-encoded extension products comprising sequence complementary to segments of the target polynucleotide. The resulting extension products can remain bound to the primer array (e.g., template and/or recipient oligo array). The resulting extension products can comprise PCR primer sites, barcode sequences, and adaptor sequences present in the original array-bound primers as well as sequence complementary to a segment of the target polynucleotide.

In some cases, primers (e.g., oligo) on a primer array (e.g., template and/or recipient oligo array) hybridize or couple to stretched target polynucleotides at primer binding sites introduced into the target polynucleotides using the methods provided herein. The hybridized or coupled primers (e.g., oligos) can be used to conduct extension reactions.

For example, in a first step, a non-array bound primer hybridizes to a target polynucleotide, which can be stretched prior to hybridization using any of the methods provided herein. Hybridization between the non-array bound primer and the target polynucleotide can be facilitated through a random sequence on the non-array bound primer and a sequence complementary to the random sequence on the target polynucleotide. Following hybridization, the hybridized non-array bound primer can be extended using any of the polymerases provided herein using the target polynucleotide as template in order to generate extension products complementary to the target polynucleotide. The non-array bound primer can further comprise a primer binding site such that the primer binding site does not hybridize to the target polynucleotide. The primer binding site can comprise defined sequence. The defined sequence can be universal, adaptor, PCR primer and/or barcode sequence. The primer binding site can comprise universal, adaptor, PCR primer and/or barcode sequence. The barcode sequence can encode positional information in a manner described herein. In some cases, the polymerase used comprises strand displacement activity. In some cases, the polymerase used does not comprise strand displacement activity. The extension products can be contacted with a primer array (e.g., template and/or recipient oligo array) comprising primer regions.

Each of the primer regions can comprise primers (e.g., oligos) bound to the primer array in one of the primer regions. Each of the array-bound primers (e.g., oligos) can comprise sequence that is complementary to the primer binding site and can thus tether the extension products as provided to the substrate upon hybridization to the primer binding site to generate array-bound extension products. Alternatively, during the extension reaction template switching can occur from the free primer to the target polynucleotide, allowing the extension product to incorporate sequence complementary to a segment of target polynucleotide.

In some cases, extension products are generated from array-bound primers coupled to a target polynucleotide comprising primer binding sites introduced by transposon insertion as provided herein. The barcode sequence can encode positional information in a manner described herein.

Extension reactions can be conducted with enzymes, such as any DNA polymerase as provided herein. The polymerase can include, but are not limited to, PolI, PolII, PolII, Klenow, T4 DNA Pol, modified T7 DNA Pol, mutated modified T7 DNA Pol, TdT, Bst, Taq, Tth, Pfu, Pow, Vent, Pab, Phusion, and Phi-29. For example, extension reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20). Extension reactions can be conducted with reverse transcriptase enzymes. In some cases, the template nucleic acid comprises RNA, and enzymatic extension reactions elongate the primer using the RNA as template. Conducting extension reactions with array-bound primers and target polynucleotide can generate array-bound extension products, comprising sections of template nucleic acid sequence or its complement and a barcode tag sequence as provided herein.

In some cases, extension products are generated from array-bound primers on an array as provided herein coupled to a target polynucleotide comprising primer binding sites introduced by nicking the target polynucleotide using a nicking enzyme and subsequently appending the primer binding sites. The nicking enzyme can be any nicking enzymes as provided herein. In some cases, the nicking enzyme is Nt.CviPII. Appendage of the priming binding sites can be through ligation. Ligation can be any ligation method as described herein. Stretching of the target polynucleotide can be any stretching method provided herein. In some cases, a target polynucleotide is stretched using molecular combing. The target polynucleotide comprising appended primer binding sites can be stretched on an oligo array using molecular combing such that one or more primer binding sites comprise sequence complementary to an oligo on an oligo array. The oligo array can be prepared by the methods provided herein. The oligo array can be a template or recipient array. The recipient array can be generated using a transfer method as provided herein. The transfer method can be a face-to-face enzymatic transfer method as provided herein. In some cases, a primer binding site on a target polynucleotide stretched on an oligo array binds to an oligo comprising a complementary sequence such that the strand of the target polynucleotide comprising the bound primer binding site serves a template for extension using a polymerase of the oligo comprising the complementary sequence, thereby generating an array bound double stranded target polynucleotide. Stretching of the target polynucleotide can through the use of molecular combing. The barcode can be a positional barcode as provided herein.

Primer extension can be conducted with Vent exo-polymerase, a thermostable enzyme, in the presence of modified nucleotides (labeled with fluorophores) which can serve to visually confirm polymerase extension. However, one of skill in the art can appreciate that any suitable polymerase enzyme as provided herein can be used. In some cases, a polymerase comprising strand displacing properties is used. The strand displacing polymerase can be Vent exo polymerase as well as phi29 and Bst. In some cases, fragmentation can be achieved through methods known in the art. Fragmentation can be through physical fragmentation methods and/or enzymatic fragmentation methods. Physical fragmentation methods can include nebulization, sonication, and/or hydrodynamic shearing. In some cases, the fragmentation can be accomplished mechanically comprising subjecting the nucleic acid to acoustic sonication. In some cases, the fragmentation comprises treating the nucleic acid with one or more enzymes under conditions suitable for the one or more enzymes to generate breaks in the double-stranded nucleic acid. Examples of enzymes useful in the generation of nucleic acid fragments include sequence specific and non-sequence specific nucleases. Non-limiting examples of nucleases include DNase I, Fragmentase, restriction endonucleases, variants thereof, and combinations thereof. Reagents for carrying out enzymatic fragmentation reactions are commercially available (e.g., from New England Biolabs). For example, digestion with DNase I can induce random double-stranded breaks in DNA in the absence of $Mg^{++}$ and in the presence of $Mn^{++}$. In some cases, fragmentation comprises treating the target polynucleotides with one or more restriction endonucleases. Fragmentation can produce fragments having 5' overhangs, 3' overhangs, blunt ends, or a combination thereof. In some cases, such as when fragmentation comprises the use of one or more restriction endonucleases, cleavage of the target polynucleotide leaves overhangs having a predictable sequence. In some cases, the fragmented double stranded target polynucleotide is end-repaired as provided herein, thereby generating blunt ends. In some cases, the fragmented double stranded target polynucleotide is end-repaired as provided herein and subsequently subjected to an A-tailing reaction as provided herein. Release of the double stranded target polynucleotide from the oligo array can be accomplished by fragmentation of the double stranded target polynucleotide from the oligo array substrate. Fragmentation can be by the use of any of the methods provided herein. In some cases, the array-bound primers (oligos) preferably have a restriction site in their 5' or 3' end, which is incorporated into the double stranded target polynucleotide and allows for the selective cleavage and release of the double stranded target polynucleotide or part thereof. In some cases, the double stranded target polynucleotide is enzymatically cleaved using NEB fragmentase. In some cases, the bond between the double stranded target polynucleotide and the primer substrate can be broken with thermal energy. In some cases, the double stranded target polynucleotide can be detached from the primer substrate by mechanical breakage or shear. Appending of the adapter to the fragmented double stranded target polynucleotide can comprise ligation. Ligation can be through any method of ligation proved herein. In some cases, the adapter appended to the double stranded target polynucleotide comprises a sequence compatible with a next generation sequencing platform (NGS) as provided herein. In some cases, the sequencing platform is an Illumina platform. In some cases, the adapter appended to the double stranded target polynucleotide comprises an Illumina primer sequence for use in the Illumina HiSeq 2500. The Illumina primer sequence can be a second Illumina primer. The released double stranded target polynucleotide can be sequenced using any sequencing method known in the art. In some cases, the released double stranded target polynucleotide is sequenced using a NGS method. The NGS method can be any NGS method as provided herein.

Polymerase Extension Optimization.

Primer extensions can be performed with a range of polymerases. For example, primer extensions have been tested with Vent exo-polymerase (see, e.g., FIG. 4B) and Bst polymerase (see, e.g., FIG. 5). Both of these polymerases have strand displacing properties, which can be important. Other polymerase enzymes can be used, such as phi-29. Thermostable polymerase enzymes can be used to allow for thermal cycling, if needed.

Extension reactions can be conducted with enzymes, such as any DNA polymerase as provided herein. The polymerase can include, but are not limited to, PolI, PolII, PolII, Klenow, T4 DNA Pol, modified T7 DNA Pol, mutated modified T7 DNA Pol, TdT, Bst, Taq, Tth, Pfu, Pow, Vent, Pab, Phusion, and Phi-29. For example, extension reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM (NH$_4$)$_2$SO$_4$, 50 mM KCl, 2 mM MgSO$_4$, and 0.1% Tween 20). Extension reactions can be conducted with reverse transcriptase enzymes. In some cases, the template nucleic acid comprises RNA, and enzymatic extension reactions elongate the primer using the RNA as template. Conducting extension reactions with array-bound primers and target polynucleotide can generate array-bound extension products, comprising sections of template nucleic acid sequence or its complement and a barcode tag sequence as provided herein.

Automated Library Preparation

Techniques of the present disclosure can automate sequencing library preparation steps. Specifically, techniques of the present disclosure can capture and immobilize long genomic DNA regions and selectively sequence regions with epigenetic modifications. The epigenetic modifications can be within the short sequence reads obtained. The immobilized genomic DNA can provide a megabase scaffold from which to hang the short reads, thereby localizing and phasing epigenetic modifications on single molecules across long genomic DNA regions. The basic approach can involve stretching many individual DNA molecules on a surface (e.g., 30-40× diploid genome coverage). The ends of the long DNA molecules can be captured and a spatially localized library can be constructed. The sequence between the ends can be probed for epigenetic modifications (e.g., 5-methylcytosine) and sequencing libraries can also be constructed for genome regions that contain epigenetic modifications. The libraries can be prepared on a spatially barcoded chip so their relative location in the genome can be determined. The NGS library can then be sequenced using any NGS platform (e.g., Illumina HiSeq). Since the primers used to generate the sequencing library are barcoded, a scaffold for assembling the short NGS reads and identifying the location of the epigenetic modifications can be obtained.

Once extension products are produced from the target polynucleotide, as described elsewhere in this disclosure, the extension products can be either sequenced directly or used to generate sequencing libraries for subsequent sequencing. In some cases, following processing of a target polynucleotide, stretching on an oligo array, and extension of the stretched target polynucleotide as provided herein, a nucleic acid library is produced. The nucleic acid library can be a sequencing library that can be produced from extension products.

In some cases, prior to sequencing, extension products produced by the methods described herein are released from an oligo array. In some cases, the bond between the extension product and the primer substrate can be broken with thermal energy. In some cases, the extension product can be detached from the primer substrate by mechanical breakage or shear. In some cases, the array-bound primers (oligos) preferably have a restriction site in their 5' or 3' end, which is incorporated into the extension product and allows for the selective cleavage and release of the extension products or part thereof. In some cases, releasing an extension product from an oligo array can be via digestion of the extension product with an enzyme for fragmenting nucleic acids as provided herein. In some cases, an extension product is released from an oligo array by digestion with restriction enzymes. The restriction enzymes can be any restriction enzymes known in the art and/or provided herein. In some cases, the extension product is enzymatically cleaved using NEB fragmentase. The digestion time for enzymatic digestion of the extension products can be adjusted to obtain select fragment sizes. In some cases, the extension products can be fragmented into a population of fragmented extension products of one or more specific size range(s). In some cases, the fragments can have an average length from about 10 to about 10,000 nucleotides or base pairs. In some cases, the fragments have an average length from about 50 to about 2,000 nucleotides or base pairs. In some cases, the fragments have an average length from about 100 to about 2,500, about 10 to about 1000, about 10 to about 800, about 10 to about 500, about 50 to about 500, about 50 to about 250, or about 50 to about 150 nucleotides or base pairs. In some cases, the fragments have an average length less than 10,000 nucleotides or bp, less than 7,500 nucleotides or bp, less than 5,000 nucleotides or bp, less than 2,500 nucleotides or bp, less than 2,000 nucleotides or bp, less than 1,500 nucleotides or bp, less than 1,000 nucleotides or bp, less than 500 nucleotides or bp, less than 400 nucleotides or bp, less than 300 nucleotides or bp, less than 200 nucleotides or bp, or less than 150 nucleotides or bp. In some cases, the fragments have an average length of about, more than, less than, or at least 10, 20, 30, 40, 50, 60, 70, 80, 90, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, or 10,000 nucleotides or base pairs.

In some cases, polynucleotide fragments generated by fragmentation of extension products on an oligo array as generated by the methods provided herein are subjected to end repair. End repair can include the generation of blunt ends, non-blunt ends (i.e. sticky or cohesive ends), or single base overhangs such as the addition of a single dA nucleotide to the 3'-end of the double-stranded nucleic acid product by a polymerase lacking 3'-exonuclease activity. In some cases, end repair is performed on the fragments to produce blunt ends wherein the ends of the fragments contain 5' phosphates and 3' hydroxyls. End repair can be performed using any number of enzymes and/or methods known in the art. An overhang can comprise about, more than, less than, or at least 1, 2, 3, 4, 5, 6, 7, 8, 9, 10, 11, 12, 13, 14, 15, 16, 17, 18, 19, or 20 nucleotides.

In some cases, extension products generated by the methods provided herein and bound to an oligo array as provided herein, remain bound to the oligo array and a sequencing library is generated from the bound extension products. The generation of a sequencing library from oligo array bound extension products generated by the methods provided herein can be by generating a second set of extension products using the array-bound extension products as templates. These second extension products can comprise a sequence complementary to the barcode sequence. The sequence complementary to the barcode sequence can be correlated to the original barcode sequence and thereby convey the same positional information as the original barcode. The second extension products can also comprise a sequence corresponding to a region or segment of the target polynucleotide, as they can be complementary to the regions of the first extension products that can be complementary to the target polynucleotide from which the array bound extension products were generated In some cases, preparation of a sequencing library from oligo array bound extension products generated by the methods provided herein is performed by hybridizing non-substrate bound primers (i.e., primers in solution or "free" primers) to the array-bound extension products and extending the hybridized non-substrate bound primers using the array bound extension products as template to generate non-array bound (or free) extension products. The non-substrate bound primers can hybridize to the array-bound extension products, for example through a random sequence segment as described herein of the non-substrate bound primer (e.g., random hexamer, etc.). The random sequence can be at least 5, 6, 7, 8, 9, 10, 11, 12, 13, 14, or 15 base pairs or nucleotides. The random sequence can be at most 5, 6, 7, 8, 9, 10, 11, 12, 13, 14, or 15 base pairs or nucleotides. Free primers can comprise PCR primer sequences. PCR primer sequences can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 base pairs or nucleotides. PCR primer sequences can be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 base pairs or nucleotides. The non-substrate bound primers can comprise adaptor sequences. The adaptor sequences can be compatible with any sequencing platforms known in the art. In some cases, the adaptor sequence comprises sequence compatible for use in Illumina NGS sequencing methods such as the Illumina HiSeq 2500 system. The adaptor sequences can be Y-shaped adaptor, or duplex or partial duplex adaptors. Extension of the non-substrate bound primers hybridized to the array bound extension product scan be conducted with enzymes, such as DNA polymerase. The polymerase can include, but are not limited to, PolI, PolI, PolII, Klenow, T4 DNA Pol, modified T7 DNA Pol, mutated modified T7 DNA Pol, TdT, Bst, Taq, Tth, Pfu, Pow, Vent, Pab, and Phi-29. For example, extension reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20).

Non-array bound extension products generated by the methods provided herein can comprise sequence corresponding to a segment of the target polynucleotide. That is, a non-array bound extension product can comprise sequence complementary to some or all of the segment of an array-bound extension product from which it was generated which can comprises sequence corresponding to or complementary to a segment of the target polynucleotide. A non-array bound extension product can comprise a barcode which comprises sequence complementary to the barcode sequence of the array-bound extension product. This complementary barcode can convey the same positional information conveyed by the original barcode sequence by correlating the complementary barcode sequence with the original barcode sequence. In a non-array bound extension product, the positional information conveyed by the barcode or complementary barcode can be correlated with the sequence corresponding to a segment of the target polynucleotide, thereby locating the segment of the target polynucleotide along the length of the stretched target polynucleotide molecule. Non-array bound extension products can comprise one or more PCR primer sequences. A non-array bound extension product can comprise a PCR primer sequence complementary to a PCR primer sequence in the array-bound extension product from which it was generated. A non-array bound extension product can comprise a PCR primer sequence from the non-array bound primer that was extended to generate the non-array bound extension product. Non-array bound extension products can comprise adaptor sequences, such as sequencing adaptors. In some cases, an adaptor sequence appended to a non-array bound extension product comprise sequence compatible for use in Illumina NGS sequencing methods such as the Illumina HiSeq 2500 system.

Extension products (non-array bound or released from an oligo array as described herein) or fragments thereof can be amplified and/or further analyzed such as by sequencing. The sequencing can be any sequencing methods known in the art. Amplification can be conducted by methods any amplification methods known in the art or provided herein. Amplification can be conducted with any enzyme as provided herein. For example, reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20). Amplification can utilize PCR primer sites incorporated into the extension products, for example from the array-bound primers (oligos) and the non-substrate bound primers. Amplification can be used to incorporate adaptors, such as sequencing adaptors, into the amplified extension products. The sequencing adaptors can be compatible with any sequencing method known in the art.

Library Amplification.

After the library molecules are transferred to the chip surface, the molecules can be sequenced on a sequencer (such as the Illumina HiSeq). The molecules can be obtained by performing linear amplification with primers directed toward a distal primer site on the immobilized molecule. However, if needed, an amplification reaction (e.g., PCR) can be performed on the chip bound DNA molecules for exponential amplification of the library.

Bioinformatics and Software

After sequencing, the sequence data can be aligned. Each sequence read can be separated into primer/tag sequence information, based on the known designed sequences of the primers/tags, and target polynucleotide information. Alignment can be aided by the encoded positional barcode information associated with each piece of target polynucleotide through its primer/tag sequence. Sequencing of the sequencing library or released extension products can generate overlapping reads with the same or adjacent barcode sequences. For example, some extension products can be long enough to reach the next specific sequence site associated with the target polynucleotide. Use of barcode sequence information can group together likely overlapping reads, which can increase accuracy and reduce computational time or effort.

In some cases, sequence reads and associated barcode sequence information obtained by the methods provided herein are analyzed by software. The sequence reads can be short (e.g., <100 bps) or long sequence reads (e.g., >100 bps). The software can perform the steps of arranging sequence reads derived from the same template. These reads can be identified by, for example, searching for reads that have barcodes from the same or neighboring columns in an oligo array comprising spot or regions as provided herein. In some cases, only reads of a certain range of distance, horizontal rows, and/or vertical columns are considered as putatively from the same template. In reading the barcodes, the software can take into account potential sequencing (and other) errors based upon barcode design. The error can be barcodes with edit distance four allows certain errors. In some cases, if a barcode contains too many errors and cannot be uniquely identified, its associate read is not directly used to assemble a sequence. While many reads can be assembled based upon relative barcode position (e.g., row numbers), some gaps can be filled by aligning reads coming from the same genomic region. One of skill in the art would appreciate that the software product can string reads together based upon barcode and can account for orientation of stretching of the target polynucleotide on an oligo array as provided herein.

For example, if DNA molecules are not strictly vertical after stretching on the DNA array, the orientation of the DNA molecules relative to the barcode columns can be analyzed by, for example, a known reference DNA sample that is spiked in. This reference DNA sample can be used to detect the relative angle of stretching, assuming the angle of stretching is similar to all the DNA molecules. For assembly of sequence reads based on comparison to a reference DNA sample (e.g. genome), such as in re-sequencing, software useful for re-sequencing assembly can be used. The software used can be compatible with the type of sequencing platform used. If sequencing is done with an Illumnia system, software packages such as Partek, Bowtie, Stampy, SHRiMP2, SNP-o-matic, BWA, BWA-MEM, CLC workstation, Mosaik, Novoalign, Tophat, Splicemap, MapSplice, Abmapper. ERNE-map (rNA), and mrsFAST-Ultra can be used. For SOliD based NGS sequencing, Bfast, Partek, Mosaik, BWA, Bowtie, and CLC workstation can be used. For 454 based sequencing, Partek, Mosaic, BWA, CLC workstation, GSMapper, SSAHA2, BLAT, BWA-SW, and BWA-MEM can be used. For Ion torrent based sequencing, Partek, Mosaic, CLC workstation, TMAP, BWA-SW, and BWA-MEM can be used. For de novo assembly of sequence reads obtained from the methods provided herein, any alignment software known in the art can be used. The software used can use an overlap layout approach for longer reads (i.e., >100 bps) or a de Bruijn graph based k-mer based approach for shorter reads (i.e., <100 bp reads). The software used for de novo assembly can be publically available software (e.g., ABySS, Trans-ABySS, Trinity, Ray, Contrail) or commercial software (e.g., CLCbio Genomics Workbench).

The above description discloses several methods and systems of the present invention. This invention is susceptible to modifications in the methods and materials, as well as alterations in the fabrication methods and equipment. Such modifications will become apparent to those skilled in the art from a consideration of this disclosure or practice of the invention disclosed herein. For example, the invention has been exemplified using nucleic acids but can be applied to other polymers as well. Consequently, it is not intended that this invention be limited to the specific embodiments disclosed herein, but that it cover all modifications and alternatives coming within the true scope and spirit of the invention.

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. In describing the invention herein, references to any element in the singular will include references to plural, and vice versa, unless it is clear from the context that this was explicitly not intended. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated herein by reference in its entirety for all purposes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for analyzing an epigenetic modification comprising:
   (a) stretching DNA comprising an epigenetic modification on a first surface;
   (b) labeling said epigenetic modification with an affinity agent that binds to said epigenetic modification;
   (c) capturing said DNA on a second surface by binding said affinity agent to said second surface, wherein said second surface comprises oligonucleotides, each oligonucleotide comprising a positional barcode sequence indicative of a location of said oligonucleotide on said second surface; and
   (d) preparing a sequencing library from said DNA, wherein a nucleic acid molecule of said sequencing library comprises (i) epigenetic information and (ii) positional barcode sequence information.

2. The method of claim 1, wherein said affinity agent comprises an antibody.

3. The method of claim 1, wherein said affinity agent comprises biotin.

4. The method of claim 2, wherein said capturing comprises binding said antibody with streptavidin.

5. The method of claim 1, wherein said preparing said sequencing library comprises using in vitro transposition.

6. The method of claim 1, wherein said positional barcode sequence is indicative of said location of said oligonucleotide on said second surface to within 0.1 μm, 0.2 μm, 0.5 μm, 1 μm, or 2 μm.

7. The method of claim 1, further comprising sequencing said sequencing library to generate sequence reads, and assembling said sequence reads with the aid of said positional barcode sequence information.

8. The method of claim 1, wherein said stretching DNA comprises combing.

9. The method of claim 1, wherein said DNA is from a genome, and wherein said stretching DNA on said first surface results in said DNA being stretched on said first surface at a density of at least 20 genomes per square centimeter.

10. The method of claim 1, wherein said DNA is from a genome, and wherein said stretching DNA on said first surface results in said DNA being stretched on said first surface at a density of at least 30× diploid genome coverage.

11. The method of claim 1, wherein said first surface is hydrophobic.

12. The method of claim 1, wherein said first surface comprises polylysine.

13. The method of claim 1, wherein said DNA comprises genomic DNA.

14. The method of claim 1, wherein said DNA is at least 1 megabase (Mb) in length.

* * * * *